US012318358B2

(12) United States Patent
Rouach et al.

(10) Patent No.: US 12,318,358 B2
(45) Date of Patent: Jun. 3, 2025

(54) PROBENECID FOR USE IN TREATING EPILEPTIC DISEASES, DISORDERS OR CONDITIONS

(71) Applicants: PARIS SCIENCES ET LETTRES—QUARTIER LATIN, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR); SORBONNE UNIVERSITÉ, Paris (FR); APHP (ASSISTANCE PUBLIQUE—HÔPITAUX DE PARIS), Paris (FR); COMMISSARIAT À L'ÉNERGIE ATOMIQUE ET AUX ÉNERGIES ALTERNATIVES (CEA), Paris (FR); UNIVERSITE DE PARIS, Paris (FR)

(72) Inventors: Nathalie Rouach, Paris (FR); Eléna Dossi, Boulogne-Billancourt (FR); Gilles Huberfeld, Garches (FR)

(73) Assignees: PARIS SCIENCES ET LETTRES, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR); SORBONNE UNIVERSITÉ, Paris (FR); APHP (ASSISTANCE PUBLIQUE HÔPITAUX DE PARIS), Paris (FR); COMMISSARIAT À L'ÉNERGIE ATOMIQUE ET AUX ÉNERGIES ALTERNATIVES (CEA), Paris (FR); UNIVERSITÉ PARIS CITÉ, Paris (FR)

( * ) Notice: Subject to any disclaimer, the term of this patent is extended or adjusted under 35 U.S.C. 154(b) by 142 days.

(21) Appl. No.: 16/630,114

(22) PCT Filed: Jul. 13, 2018

(86) PCT No.: PCT/EP2018/069092
§ 371 (c)(1),
(2) Date: Jan. 10, 2020

(87) PCT Pub. No.: WO2019/012109
PCT Pub. Date: Jan. 17, 2019

(65) Prior Publication Data
US 2020/0163916 A1 May 28, 2020

(30) Foreign Application Priority Data
Jul. 13, 2017 (EP) .................... 17305934

(51) Int. Cl.
*A61K 31/195* (2006.01)
*A61P 25/08* (2006.01)
*A61K 9/00* (2006.01)

(52) U.S. Cl.
CPC ............ *A61K 31/195* (2013.01); *A61P 25/08* (2018.01); *A61K 9/0019* (2013.01); *A61K 9/0053* (2013.01)

(58) Field of Classification Search
CPC ............................. A61K 31/165; A61P 25/08
USPC ........................................................ 514/562
See application file for complete search history.

(56) References Cited

U.S. PATENT DOCUMENTS

| | | | |
|---|---|---|---|
| 4,657,899 A | 4/1987 | Rzeszotarski et al. |
| 4,705,781 A | 11/1987 | Boast |
| 4,746,653 A | 5/1988 | Hutchison et al. |
| 4,761,405 A | 8/1988 | Rzeszotarski et al. |
| 4,812,458 A | 3/1989 | Honoré et al. |
| 4,863,953 A | 9/1989 | Leeson et al. |
| 4,889,855 A | 12/1989 | Jacobsen et al. |
| 4,898,854 A | 2/1990 | Hutchison et al. |
| 4,902,687 A | 2/1990 | Ornstein |
| 4,902,695 A | 2/1990 | Ornstein |
| 4,904,681 A | 2/1990 | Cordi et al. |
| 4,906,621 A | 3/1990 | Hutchison et al. |
| 4,918,064 A | 4/1990 | Cordi et al. |
| 4,925,867 A | 5/1990 | Baker et al. |
| 4,960,786 A | 10/1990 | Salituro et al. |
| 4,968,678 A | 11/1990 | Ornstein |

(Continued)

FOREIGN PATENT DOCUMENTS

| | | |
|---|---|---|
| EP | 0 260 467 B1 | 3/1988 |
| EP | 0 275 820 B1 | 7/1988 |

(Continued)

OTHER PUBLICATIONS

Neurological disorders, John Hopkins Medicine, https://www.hopkinsmedicine.org/health/conditions-and-diseases/neurological-disorders, accessed Jul. 31, 2021.*
Enna et al. Journal of Neurochemistry 1977, 28, 1121-1124.*
Moroni et al. Journal of Neurochemistry 1988, 51, 177-180.*
Vecsei et al. Brain Research Bulletin 1992, 28 (2), 233-238.*
Thurman et al. Epilepsia 2011, 52 (Suppl. 7), 2-26.*
Silverman et al. Am J Physiol Cell Physiol 2008 295 (3) C761-C767.*
Santiago et al. PLOS One 20011, 6 (9), e25178, p. 1-8.*
Bhaskaracharya et all. PLOS One 2014, 9 (3), e93058, pp. 1-8.*
Li et al. Oncotarget 2017, 8(4), 6883.*
Fauser et al. Brain 2006, 129, 1907-1916.*

(Continued)

*Primary Examiner* — Irina Neagu
(74) *Attorney, Agent, or Firm* — Maier & Maier, PLLC

(57) ABSTRACT

Probenecid or a pharmaceutical acceptable salt thereof for use in the treatment of a neurological disorder in a subject in need thereof, wherein administration of probenecid or a pharmaceutical acceptable salt thereof controls clinical or electrographic seizures in the subject. Preferably, the neurological disorder is an epileptic disease, disorder or condition.

13 Claims, 3 Drawing Sheets

(56) References Cited

U.S. PATENT DOCUMENTS

| | | | | |
|---|---|---|---|---|
| 5,489,579 | A | * | 2/1996 | McDonald .............. A61P 25/08 514/85 |
| 5,627,168 | A | * | 5/1997 | Bigge .................. A61K 31/675 514/85 |

FOREIGN PATENT DOCUMENTS

| | | |
|---|---|---|
| EP | 0 302 826 A2 | 2/1989 |
| EP | 0 303 387 B1 | 2/1989 |
| EP | 0 315 959 B1 | 5/1989 |
| EP | 0 342 558 B1 | 11/1989 |
| EP | 0 348 872 B1 | 1/1990 |
| EP | 0 364 996 A2 | 4/1990 |
| EP | 0 374 534 B1 | 6/1990 |
| EP | 0 377 112 B1 | 7/1990 |
| EP | 0 3781 34 A2 | 7/1990 |
| EP | 0 386 839 B1 | 9/1990 |
| EP | 0 387 867 B1 | 9/1990 |
| EP | 0 391 850 B1 | 10/1990 |
| EP | 0 396 124 A2 | 11/1990 |
| EP | 0 418 863 B1 | 3/1991 |
| EP | 0 420 806 B1 | 4/1991 |
| EP | 0501378 A1 | 9/1992 |
| EP | 0 603 301 B1 | 6/1994 |
| GB | 2104078 B | 1/1985 |
| GB | 2 157 685 A | 10/1985 |
| GB | 2156818 B | 10/1987 |
| GB | 2 198 134 B | 7/1990 |
| GB | 2 231 048 A | 11/1990 |
| GB | 2 201 676 B | 1/1991 |
| JP | 586027 A | 4/1993 |
| JP | 6510544 A | 11/1994 |
| JP | 7504890 A | 6/1995 |
| WO | 93/04688 A1 | 3/1993 |
| WO | 9312780 A1 | 7/1993 |

OTHER PUBLICATIONS

Anand K. Sarma, et al., "Medical management of epileptic seizures: challenges and solutions", Neuropsychiatric Disease and Treatment, 2016, vol. 12, pp. 467-485 (19 pgs.).

Stephen M. Berge, et al., "Pharmaceutical Salts", Journal of Pharmaceutical Sciences, Jan. 1977, vol. 66, No. 1, pp. 1-19 (19 pgs.).

Anne T. Berg, et al., "Revised terminology and concepts for organization of seizures and epilepsies: Report of the LAE Commission on Classification and Terminology, 2005-2009", Epilepsia, 2010, vol. 51, No. 4, pp. 676-685 (10 pgs.).

Elena Dossi, et al., "Multi-electrode Array Recordings of Human Epileptic Postoperative Cortical Tissue", Journal of Visualized Experiments (JOVE), Oct. 2014, vol. 92, e51870, pp. 1-9 (9 pgs.), at URL: http://www.jove.com/video/51870.

H. Németh, et al., "Kynurenine administered together with probenecid markedly inhibits pentylenetetrazol-induced seizures. An electrophysiological and behavioural study", Neuropharmacology, 2004, vol. 47, No. 6, pp. 916-925 (10 pgs.).

Charles P. Taylor, et al., "Probenecid pretreatment enhances anticonvulsant action of NBQX in mice", European Journal of Pharmacology, 1992, vol. 213, No. 1, pp. 151-153 (3 pgs.).

Rachel A. Bergstrom, et al., "Automated identification of multiple seizure-related and interictal epileptiform event types in the EEG of mice", Science Reports, Mar. 21, 2013, vol. 3, No. 1483, pp. 1-8 (8 pgs.).

Matthias A. Hediger, et al., "Molecular Physiology of Urate Transport", Physiology (Bethesda), Apr. 2005, vol. 20, pp. 125-133 (9 pgs.).

Ana Laura Colín-González, et al., "Probenecid : An Emerging Tool for Neuroprotection", CNS & Neurological Disorders—Drug Targets, 2013, vol. 12, No. 7, pp. 1050-1065 (16 pgs.).

Alan C. Foster, et al., "Kynurenic Acid Blocks Neurotoxicity and Seizures Induced in Rats by the Related Brain Metabolite Quinolinic Acid", Neuroscience Letters, 1984, vol. 48, pp. 273-278 (6 pgs.).

David W. Walker, et al., "Kynurenic Acid in Brain and Cerebrospinal Fluid of Fetal, Newborn, and Adult Sheep and Effects of Placental Embolization", Pediatric Research, 1999, vol. 45, No. 6, pp. 820-826 (7 pgs.).

William Silverman, et al., "Probenecid, a gout remedy, inhibits pannexin 1 channels", Am J Physiol Cell Physiol, 2008, vol. 295, No. 3, pp. C761-C767 (7 pgs.).

Weihong MA, et al., "Pharmacological Characterization of Pannexin-1 Currents Expressed in Mammalian Cells", The Journal of Pharmacology and Experimental Therapeutics, 2009, vol. 328, No. 2, pp. 409-418 (10 pgs.).

Arthur Yuwiler, et al., "Is There a Probenecid Sensitive Transport System for Monoamine Catabolites at the Level of the Brain Capillary Plexus?", Neurochemical Research, 1982, vol. 7, No. 10, pp. 1277-1285 (9 pgs.).

International Search Report dated Aug. 20, 2018, in connection with corresponding international Application No. PCT/EP2018/069092 (4 pgs.).

Gong, "The role of probenecid in the treatment of refractory epilepsy by reversing the expression of multidrug resistance-associated protein", Journal of Stroke and Neuropathy, Dec. 2005, vol. 22 No. 6, 10 pages.

* cited by examiner

PROBENECID FOR USE IN TREATING EPILEPTIC DISEASES, DISORDERS OR CONDITIONS

FIELD

The present invention relates to the treatment of epileptic diseases, disorders or conditions in human subjects. In particular, the present invention relates to the use of probenecid or of a pharmaceutically acceptable salt thereof for treating an epileptic disease, disorder or condition.

BACKGROUND

Epilepsy comprises a group of neurological disorders characterized by the periodic occurrence of seizures, which compromise proper brain functioning. Despite being one of the most common neurologic illness, affecting approximately 1% of the population worldwide, no effective universal cure is currently available and up to 30% of the patients are not controlled by current drugs.

Pharmacological therapies that are able to successfully control seizures are mainly based on three different general strategies (Sarma et al., Neuropsychiatr Dis Treat. 2016; 12: 467-485):

(1) the limitation of neuronal firing by blocking ion channels, such as voltage-gated $Na^+$, $K^+$ and $Ca^{2+}$ channels, or NMDA and AMPA glutamate receptors, using drugs such as, for example, topiramate, lamotrigine, oxcarbazepine or pregabalin;

(2) the enhancement of the activity of inhibitory synapses by GABA receptor activation or GABA reuptake inhibition, using, for example, felbamate, vigabatrin or tiagabine; and (3) the control of neurotransmitter release, using neuromodulators such as, e.g., levetiracetam.

However, current antiepileptic drugs (AEDs) present various and eventually severe side effects, due to their action on ubiquitously expressed channels and receptors, which are involved in many physiological processes (Sarma et al., Neuropsychiatr Dis Treat. 2016; 12: 467-485). Indeed, it has been reported that currently available AEDs can cause aplastic anemia and hepatic failure (e.g., felbamate), paresthesia, metabolic acidosis and glaucoma (topiramate), as well as somnolence, dizziness (e.g., tiagabine and pregabalin) and behavioral and/or psychiatric abnormalities (e.g., levetiracetam, or perampanel).

Moreover, although 70% of epileptic patients are able to adequately control their symptoms (in particular seizures) with the currently available AEDs, the remaining 30% are unable to obtain seizure freedom, display intractable seizures using available AEDs, and are, as such, termed as suffering from "treatment-resistant epilepsy".

In this condition, whose mechanisms are still unclear, the surgical resection of the specific part of the brain identified as the epileptogenic zone remains the only alternative treatment giving a positive outcome to patients.

Therefore, identifying alternative targets to develop novel antiepileptic therapies has become crucial. Advances have been achieved in terms of surgical procedures and management, routes of AED administration and electroencephalography technology; however, managing epileptic patients still remains challenging due to the complex nature of the disease, AED side effects, drug interactions, death risk and medical and/or psychiatric comorbidities. Furthermore, specific patient categories, such as children, pregnant women, elderly, psychiatric and HIV/AIDS patients, are even more difficult to manage.

Probenecid is a highly lipid soluble benzoic acid derivative with an excellent safety profile that was developed in the 1950's to decrease the renal tubular excretion of penicillin; and has been used to increase the serum concentration of several antibiotics and antivirals. During the initial studies using probenecid (referred to as Benemid), probenecid was observed to have a strong uricosuric effect and quickly became the standard of treatment of gout. It was found to decrease uric acid levels in the serum via inhibition of organic acid reabsorption, such as uric acid, by the renal proximal tube by acting as a competitive inhibitor of the organic anion transporters (OATs) and thus preventing OAT-mediated reuptake of uric acid from the urine to the serum. Even though probenecid has a minimal adverse effect profile, its clinical use has declined significantly as other therapies for gout have shown improved efficacy.

Surprisingly, the Inventors have demonstrated that probenecid was able to block epileptic seizures in epileptic cortical human tissues ex vivo, and in the kainate mouse models of temporal lobe epilepsy in vivo, paving the way for a novel, low-side-effect, antiepileptic therapy.

The present invention thus relates to the use of probenecid for treating an epileptic disease, disorder or condition in a subject.

SUMMARY

The present invention relates to probenecid or a pharmaceutical acceptable salt thereof for use in the treatment of a neurological disorder in a subject in need thereof.

In one embodiment, administration of probenecid or a pharmaceutical acceptable salt thereof inhibits electrographic seizures in said subject.

In one embodiment, administration of probenecid or a pharmaceutical acceptable salt thereof inhibits compulsive behaviors in said subject.

In one embodiment, administration of probenecid or a pharmaceutical acceptable salt thereof controls clinical or electrographic seizures in said subject.

In one embodiment, the neurological disorder is an epileptic disease, disorder or condition.

In one embodiment, the epileptic disease, disorder or condition is selected from the group consisting of familial epilepsy, genetic epilepsy, structural/metabolic epilepsy, as well as epilepsies with no discovered cause.

In one embodiment, the epileptic disease, disorder or condition is brain tumor-related epilepsy.

In another embodiment, the epileptic disease, disorder or condition is a malformation of cortical development (MCD)-related epilepsy.

In another embodiment, the epileptic disease, disorder or condition is a neurodegenerative-related epilepsy.

In another embodiment, the epileptic disease, disorder or condition is a dysimmune epilepsy.

In another embodiment, the epileptic disease, disorder or condition is a glioma-related epilepsy.

In one embodiment, said subject is suffering from a treatment-resistant epileptic disease, disorder or condition.

In one embodiment, the subject is a child. In one embodiment, said subject is an adult.

In one embodiment, probenecid or the pharmaceutical acceptable salt thereof is to be administered to the subject at a dose ranging from about 1 mg/kg/day to about 100 mg/kg/day.

In one embodiment, probenecid or the pharmaceutical acceptable salt thereof is to be administered orally or by injection.

The present invention also relates to a pharmaceutical composition comprising probenecid or a pharmaceutical acceptable salt thereof and a pharmaceutically acceptable carrier or diluent, for use in the prevention or the treatment of an epileptic disease, disorder or condition in a subject in need thereof.

The present invention further relates to a medicament comprising probenecid or a pharmaceutical acceptable salt thereof, for use in the prevention or the treatment of an epileptic disease, disorder or condition in a subject in need thereof.

DETAILED DESCRIPTION

Figure 1A:
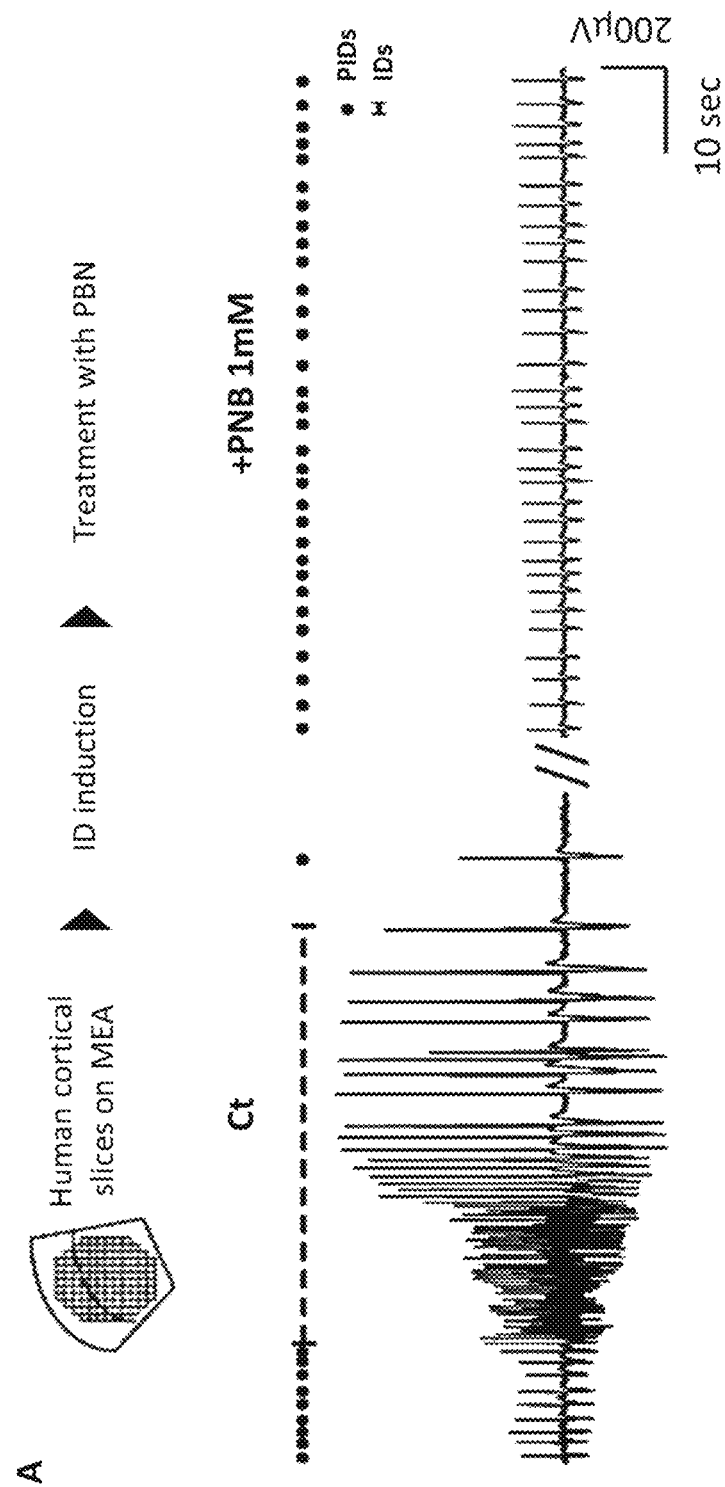
FIG. 1A (Top), is a schematic representation of the experimental protocol: human cortical slices placed on MEA are incubated in pro-epileptic conditions to induce ictal-like discharges (IDs); after ID induction, PBN is applied. (Bottom), example of ID activity recorded from a human epileptic cortical slice before (left) and after (right) the treatment with PBN (1 mM, 30 min). When Panx1 channels are blocked by PBN, IDs (black dashed line) disappear, but not PIDs (black filled dots, respectively).
Figure 1B:
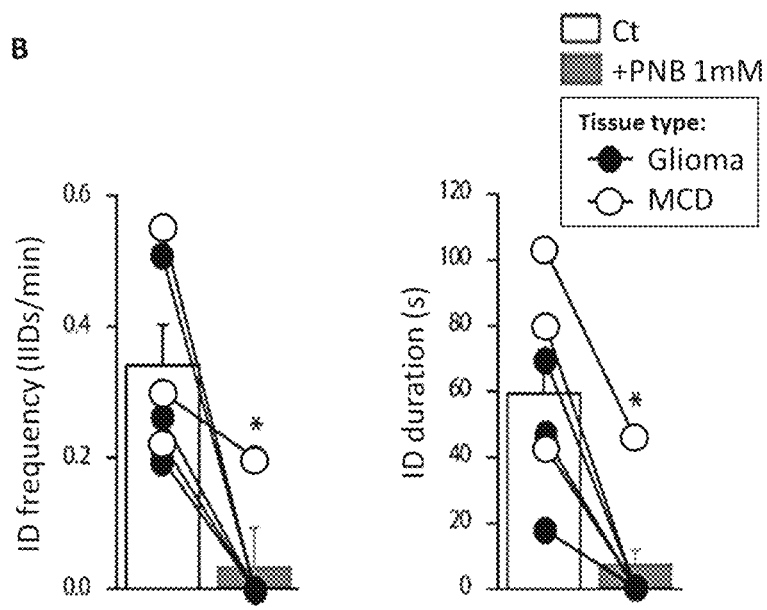
FIG. 1B is a graph depicting the quantification of PBN effect on ID frequency and duration (p=0.0313, n=6 slices from 2 gliomas and 2 MCD patients, Wilcoxon matched pairs test). Glioma and MCD slice values are indicated in black and grey filled circles, respectively.

In the present invention, the following terms have the following meanings:

"About" preceding a value means plus or less 10% of said value.

As used herein, the term "consist essentially of probenecid or a pharmaceutically acceptable salt thereof", with reference to a composition, pharmaceutical composition or medicament, is intended to mean that probenecid or the pharmaceutically acceptable salt thereof is the only therapeutic agent, i.e., the only agent exhibiting a biologic activity, within said composition, pharmaceutical composition or medicament.

As used herein, the terms "epilepsy", "epileptic disease, disorder or condition" and "epileptic syndrome" are interchangeable and refer to a disease, disorder or condition characterized by the occurrence of epileptic seizures, preferably of spontaneous and/or recurrent seizures.

As used herein, the terms "epileptic seizure" or "ictal event" refer to an episodic change in the behavior or feeling or consciousness caused by the disordered firing of populations of neurons of the central nervous system (CNS), resulting in varying degrees of any of involuntary muscle contraction, abnormal perceptions, abnormal behaviors, alteration of consciousness and/or loss of consciousness.

As used herein, the term "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

As used herein, the term "pharmaceutically acceptable salts" is meant to include salts of probenecid that are prepared with relatively nontoxic acids or bases. Examples of pharmaceutically acceptable base addition salts include, but are not limited to, sodium, potassium, calcium, ammonium, organic amino, or magnesium salt, or a similar salt. Examples of pharmaceutically acceptable acid addition salts include, but are not limited to, those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, e.g., Berge et al., J Pharm Sci. 1977 January; 66(1):1-19).

Non-limiting examples of probenecid salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). Other examples of probenecid salts include, but are not limited to, probenecid sodium, probenecid potassium, probenecid magnesium, probenecid bismuth, probenecid cerium tetrahydrate, probenecid cerium trihydrate, probenecid erbium trihydrate, probenecid europium trihydrate, probenecid holmium trihydrate, probenecid lanthanum trihydrate, probenecid lutetium hexahydrate, probenecid samarium trihydrate, probenecid terbium trihydrate, probenecid thallium trihydrate, probenecid thulium trihydrate, probenecid yttrium hexahydrate and probenecid styrene. Preferably, probenecid salts are chosen from the group consisting of probenecid sodium, probenecid potassium and probenecid magnesium. These salts may be prepared by methods known to those skilled in the art.

As used herein, the term "probenecid" refers to a compound having formula (I):

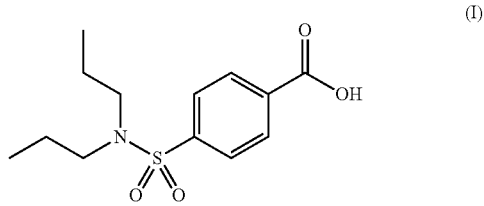 [SMILES: CCCN(CCC)S(=O)(=O)c1ccc(C(=O)O)cc1]

(I)

Probenecid encompasses free-base probenecid (sometimes also referred to as 4-(dipropylsulfamoyl)benzoic acid, 4-[(dipropylamino)sulfonyl]-benzoic acid or PBN), as well as pharmaceutically acceptable salts thereof (4-(dipropylsulfamoyl)benzoate salts or 4-[(dipropylamino)sulfonyl]-benzoate salts). Also encompassed are prodrugs, isomers, and polymorphs of probenecid. Probenecid can exist in unsolvated forms as well as solvated forms, including hydrated forms. In general, the solvated forms are equivalent to unsolvated forms and are encompassed within the scope of the present invention. Probenecid may exist in multiple crystalline or amorphous forms. In general, all physical forms are equivalent for the uses contemplated by the present invention and are intended to be within the scope of the present invention.

As used herein, the term "prodrug" refers to a probenecid analogue that readily undergoes chemical changes under physiological conditions to provide active probenecid. Prodrugs of probenecid may be converted in vivo after administration. Additionally, prodrugs of probenecid can be converted to active probenecid by chemical or biochemical methods in an ex vivo environment, such as, for example, when contacted with a suitable enzyme or chemical reagent.

As used herein, the term "subject" refers to an animal, preferably a warm-blooded animal, more preferably a mammal, even more preferably a human. In one embodiment, a subject may be a mammal. Mammals include, but are not limited to, all primates (human and non-human), cattle (including cows), horses, pigs, sheep, goats, dogs, and cats. In one embodiment, the subject is a human. In one embodiment, the subject is a patient, i.e., is awaiting the receipt of, or is receiving medical care or was/is/will be the object of a medical procedure, or is monitored for the development of an epileptic disease, disorder or condition. In one embodiment, the subject is an adult (for example a subject above the age of 18). In another embodiment, the subject is a child (for example a subject below the age of 18). In one embodiment, the subject is a male. In another embodiment, the subject is a female.

As used herein, "substantially healthy subject" refers to a subject who has not been previously diagnosed or identified as having or suffering from an epileptic disease, disorder or condition. In one embodiment, a substantially healthy subject shows no onset of an epileptic disease, disorder or condition, i.e., the subject has not yet acquired, developed, or first experienced epileptic seizures.

As used herein, the terms "treating" or "treatment" or "alleviation" refers to both therapeutic treatment and prophylactic or preventative measures; wherein the object is to prevent or slow down (lessen) the targeted pathologic condition or disorder, such as for example an epileptic disease, disorder or condition. Those in need of treatment include those already with the disease, disorder or condition as well as those prone to have the disease, disorder or condition, or those in whom the disease, disorder or condition is to be prevented. A subject is successfully "treated" for a specific disease, disorder or condition, such as for example an epileptic disease, disorder or condition if, after receiving a therapeutic amount of probenecid according to the present invention, the subject shows observable and/or measurable reduction in one or more of the followings: epileptic seizures, in particular clinical epileptic seizures (that may be completely absent); reduced morbidity and mortality; improvement in quality of life issues. The above parameters for assessing successful treatment and improvement in the disease, disorder or condition are readily measurable by routine procedures familiar to a physician.

As used herein, the terms "therapeutically effective amount" mean level or amount of agent that is aimed at, without causing significant negative or adverse side effects to the target, (1) delaying or preventing the onset of a target disease, disorder, or condition; (2) slowing down or stopping the progression, aggravation, or deterioration of one or more symptoms of the target disease, disorder, or condition; (3) bringing about ameliorations of the symptoms of the target disease, disorder, or condition; (4) reducing the severity or incidence of the target disease, disorder, or condition; or (5) curing the target disease, disorder, or condition. A therapeutically effective amount may be administered prior to the onset of the target disease, disorder, or condition, for a prophylactic or preventive action. Alternatively or additionally, the therapeutically effective amount may be administered after initiation of the target disease, disorder, or condition, for a therapeutic action.

The present invention relates to probenecid or a pharmaceutically acceptable salt thereof, for use in the treatment of a neurological disorder in a subject in need thereof. In one embodiment, said neurological disorder is associated with clinical or electrographic seizures, and the administration of probenecid or a salt thereof controls clinical or electrographic seizures in said subject. In one embodiment, said neurological disorder is associated with electrographic seizures, and the administration of probenecid or a salt thereof inhibits electrographic seizures in said subject. In one embodiment, said neurological disorder is associated with compulsive behaviors, and the administration of probenecid or a salt thereof inhibits compulsive behaviors in said subject. In a preferred embodiment, the invention relates to probenecid or a pharmaceutically acceptable salt thereof, for use in the treatment of an epileptic disease, disorder or condition.

In one embodiment, probenecid or a pharmaceutically acceptable salt thereof is for preventing a neurological disorder, preferably an epileptic disease, disorder or condition. In one embodiment, probenecid or a pharmaceutically acceptable salt thereof is for preventing electrographic seizures in said subject. In one embodiment, probenecid or a pharmaceutically acceptable salt thereof is for preventing compulsive behaviors in said subject. In one embodiment, probenecid or a pharmaceutically acceptable salt thereof is for preventing clinical or electrographic seizures in said subject.

In one embodiment, probenecid or a pharmaceutically acceptable salt thereof is for curing a neurological disorder, preferably an epileptic disease, disorder or condition.

Epilepsy, as to be understood within the scope of the present invention, is a brain disorder which is classified within the group of "episodic and paroxysmal disorders", codes G40 and G41, according to the International Statistical Classification of Diseases and Related Health Problems $10^{th}$ Revision (ICD-10).

In one embodiment, epilepsy is associated with electrographic seizures. In one embodiment, probenecid or a pharmaceutical acceptable salt thereof may inhibit electrographic seizures in a subject suffering from an epileptic disease, disorder or condition.

In one embodiment, epilepsy is associated with compulsive behaviors. In one embodiment, probenecid or a pharmaceutical acceptable salt thereof may inhibit compulsive behaviors in a subject suffering from an epileptic disease, disorder or condition.

In one embodiment, epilepsy is associated with clinical and/or electrographic seizures. In one embodiment, probenecid or a pharmaceutical acceptable salt thereof may control clinical or electrographic seizures in a subject suffering from an epileptic disease, disorder or condition.

The ILAE (International League Against Epilepsy) has published in 2010 a revised classification of epileptic diseases, disorders or conditions (Berg et al., Epilepsia. 2010 April; 51(4):676-85, which is herein incorporated by reference). According to said classification, epileptic diseases, disorders or conditions may be classified according to the seizure type, etiology, age at onset, cognitive and developmental antecedents and consequences, motor and sensory examinations, EEG features, provoking or triggering factors, and/or patterns of seizure occurrence with respect to sleep.

Seizure types include, but are not limited to, generalized seizures, focal seizures (or partial seizures), seizures with unknown onset, generalized status epilepticus and focal status epilepticus.

In one embodiment, the subject is/was diagnosed with or is at risk of developing an epileptic disease, disorder or condition with generalized seizures. Examples of generalized seizures include, but are not limited to, tonic-clonic seizures (including variations beginning with a clonic or myoclonic phase), clonic seizures (without and with tonic features), typical absence seizures, atypical absence seizures, myoclonic absence seizures, tonic seizures, spasms, myoclonic seizures, massive bilateral myoclonus, eyelid myoclonia (without and with absences), myoclonic atonic seizures, negative myoclonus and atonic seizures.

In one embodiment, the subject is/was diagnosed with or is at risk of developing an epileptic disease, disorder or condition with focal seizures. Examples of focal seizures include, but are not limited to, focal sensory seizures, focal motor seizures, gelastic seizures, hemiclonic seizures and secondarily generalized seizures.

In one embodiment, the subject is/was diagnosed with or is at risk of developing an epileptic disease, disorder or condition with focal sensory seizures. Examples of focal sensory seizures include, but are not limited to, focal sensory seizures with elementary sensory symptoms (such as, e.g., occipital lobe seizures, parietal lobe seizures), focal sensory seizures with experiential sensory symptoms (such as, e.g., temporo-parieto-occipital junction seizures).

In one embodiment, the subject is/was diagnosed with or is at risk of developing an epileptic disease, disorder or condition with focal motor seizures. Examples of focal motor seizures include, but are not limited to, focal motor seizures with elementary clonic motor signs, focal motor seizures with asymmetrical tonic motor seizures (such as, e.g., supplementary motor seizures), focal motor seizures with typical (temporal lobe) automatisms (such as, e.g., mesial temporal lobe seizures), focal motor seizures with hyperkinetic automatisms, focal motor seizures with focal negative myoclonus and focal motor seizures with inhibitory motor seizures.

In one embodiment, the subject is/was diagnosed with or is at risk of developing an epileptic disease, disorder or condition with generalized status epilepticus. Examples of generalized status epilepticus include, but are not limited to, generalized tonic-clonic status epilepticus, clonic status epilepticus, absence status epilepticus, tonic status epilepticus and myoclonic status epilepticus.

In one embodiment, the subject is/was diagnosed with or is at risk of developing an epileptic disease, disorder or condition with focal status epilepticus. Examples of focal status epilepticus include, but are not limited to, epilepsia partialis continua of Kojevnikov, aura continua, limbic status epilepticus (psychomotor status) and hemiconvulsive status.

Epileptic disease, disorder or condition can also be classified according to their etiology, i.e., their underlying cause. Etiologies of epileptic disease, disorder or condition include, but are not limited to, familial epilepsy, genetic epilepsy, structural/metabolic epilepsy and epilepsy of unknown cause.

In one embodiment, the subject has a familial history of an epileptic disease, disorder or condition. In another embodiment, the subject does not have any familial history of an epileptic disease, disorder or condition.

In one embodiment, the epileptic disease, disorder or condition is a familial focal epilepsy, that can be lesional or non-lesional. Examples of familial focal epilepsies include, but are not limited to, autosomal-dominant nocturnal frontal lobe epilepsy (ADNFLE), familial temporal lobe epilepsy (FTLE), familial mesial temporal lobe epilepsy (FMTLE), familial lateral temporal lobe epilepsy (FLTLE), familial partial epilepsy with variable foci (FPEVF), Rolandic epilepsies and benign familial partial epilepsies of childhood. Preferably, the epileptic disease, disorder or condition is selected from the group comprising autosomal-dominant nocturnal frontal lobe epilepsy (ADNFLE), familial temporal lobe epilepsy (FTLE) and familial focal epilepsy with variable foci (FFEVF).

In one embodiment, the subject has a genetic environment and/or at least one member of its family (i.e., a relative, such as, e.g., a parent [mother or father], a sibling [sister or brother], a child [daughter or son], a grandparent [grandmother or grand-father], a cousin, a niece, a nephew, an aunt, an uncle and the like), has a genetic environment prone to the development of an epileptic disease, disorder or condition.

In one embodiment, the subject and/or at least one member of its family is/was diagnosed with at least one genetic mutation in at least one allele of at least one gene known or not yet known to be involved with epileptic seizures. Examples of genetic environment prone to the development of an epileptic disease, disorder or condition include, but are not limited to, genetic mutations in at least one allele of any one of the following genes: CHRNA4, CHRNA2, CHRNB2, SCN1A, LGI1, KCNT1, ABAT, ABCB1, ADSL, ALDH7A1, ARFGEF2, ARHGEF9, ARX, ASPM, ATP1A2, ATP6AP2, ATR, BRD2, CACNA1A, CACNA1H, CACNB4, CASK, CASR, CCL2, CDK5RAP2, CDKL5, CDON, CENPJ, CEP152, CLCN2, CLN3, CLN5, CLN6, CLN8, CNTNAP2, CSTB, CTSD, DCX, EFHC1, EFHC2, EMX2, EPM2A, FLNA, FLVCR2, FOLR1, FOXG1, FOXH1, GABRA1, GABRB3, GABRD, GABRG2, GAMT, GATM, GLI2, GPR56, GRIN1, GRIN2A, HCN1, HCN3, HCN4, KCNA1, KCNAB1, KCNJ10, KCNJ11, KCNMA1, KCNQ2, KCNQ3, KCNV2, LIS1, MAGI2, MBD5, MCPH1, ME2, MECP2, MEF2C, MFSD8, MTHFR, NDE1, NDUFA1, NHLRC1, NODAL, NRXN1, 5 OPHN1, OPRM1, PAFAH1B1, PAFAH1BA, PCDH19, PCNT, PHF6, PLCB1, PNKP, PNPO, POLG, PPT1, PRICKLE1, PRICKLE2, PRRT2, PTCH1, RELN, SCN10A, SCN11A, SCN1B, SCN2B, SCN3A, SCN3B, SCN4A, SCN4B, SCN5A, SCN7A, SCN8A, SCN9A, SHH, SIX3, SLC25A19, SLC25A22, SLC2A1, SLC9A6, SPTAN1, SRPX2, STIL, STXBP1, SYN1, TCF4, TGIF1, TPP1, TSEN2, TSEN34, TSEN54, UBE3A, VANGL1, WDR62, ZEB2 and ZIC2.

In one embodiment, the epileptic disease, disorder or condition is a structural or metabolic epilepsy. In one embodiment, the structural or metabolic epilepsy is a neurological-related epilepsy. In one embodiment, the structural or metabolic epilepsy is a neurodegenerative-related epilepsy. In one embodiment, the structural or metabolic epilepsy is an injury-related epilepsy.

In one embodiment, the epileptic disease, disorder or condition results from a neurological disease and/or an injury. Examples of neurological diseases or injuries resulting in an epileptic disease, disorder or condition include, but are not limited to, brain tumor, malformations of cortical development (MCD), head or brain trauma, encephalitis, cerebritis, abscess, stroke, tuberous sclerosis, mesial temporal sclerosis, cerebral dysgenesis, hypoxic-ischemic encephalopathy, alcohol drinking, drugs and/or chemicals use, alcohol withdrawal, and drugs and/or chemicals withdrawal. In one embodiment, the neurological diseases or injuries resulting in an epileptic disease, disorder or condition is selected from brain tumor, malformations of cortical development (MCD), head or brain trauma, encephalitis, cerebritis, abscess, stroke, tuberous sclerosis, mesial temporal sclerosis, cerebral dysgenesis, hypoxic-ischemic encephalopathy, dysimmune conditions, alcohol drinking, drugs and/or chemicals use, alcohol withdrawal, and drugs and/or chemicals withdrawal.

In one embodiment, the subject is/was diagnosed with or is at risk of developing a brain tumor-related epilepsy (BTRE). BTRE include, but are not limited to, glioma-related epilepsy (including glioblastoma, glioblastoma multiforme, astrocytoma, pilocytic astrocytoma, diffuse astrocytoma, anaplastic astrocytoma, mixed astrocytoma I and II WHO, oligodendroglioma, anaplastic oligodendroglioma, ependymoma, and anaplastic ependymoma), craniopharyngioma-related epilepsy, epidermoid-related epilepsy, lymphoma-related epilepsy, meningioma-related epilepsy, schwannoma-related epilepsy, pituitary adenoma-related epilepsy, pinealoma-related epilepsy (including pineocytoma and pineoblastoma) and medulloblastoma-related epilepsy.

In one embodiment, the subject is/was diagnosed with or is at risk of developing a malformation of cortical development (MCD)-related epilepsy. MCD-related epilepsies include, but are not limited to, dysembryoplastic neuroepithelial tumour (DNET)-related epilepsy, cortical dysplasia-related epilepsy, focal cortical dysplasia (FCD)-related epilepsy (including FCD of type 1a, 1b, 2a, 2b, 3a, 3b and 3c), microcephaly-related epilepsy, hemimegalencephaly-related epilepsy, megalencephaly-related epilepsy, periventricular heterotopia-related epilepsy, classical lissencephaly-related epilepsy, subcortical band heterotopia-related epilepsy and cobblestone lissencephaly-related epilepsy.

In one embodiment, the subject is/was diagnosed with or is at risk of developing a neurodegenerative-related epilepsy. Examples of neurodegenerative-related epilepsies include, but are not limited to, Alzheimer-related epilepsy, Parkinson-related epilepsy and autism-related epilepsy.

Epileptic diseases, disorders or conditions can further be classified according to the age of the subject at onset, i.e., the age at which the subject acquires, develops, or first experiences epileptic seizures. Epileptic diseases, disorders or conditions can therefore be categorized as congenital, infantile, juvenile or adult.

In one embodiment, the epileptic disease, disorder or condition to be treated is infantile or juvenile epilepsy. Infantile and juvenile epilepsy refers to epileptic diseases, disorders or conditions as defined hereinabove, that can occur during childhood (and which last or not during adulthood). Examples of these include, but are not limited to, benign familial neonatal epilepsy (BFNE), benign neonatal seizures (BNS) (including benign familial neonatal seizures), benign neonatal familial convulsions (BFNC), myoclonic epilepsy in infancy (MEI), early myoclonic encephalopathy (EME), epilepsy of infancy with migrating focal seizures, benign childhood epilepsy, benign familial and non-familial infantile seizures, febrile seizures, infantile spasm, Ohtahara syndrome, juvenile myoclonic epilepsy, juvenile absence epilepsy, childhood absence epilepsy (e.g., pyknolepsy), early onset benign childhood occipital epilepsy (Panayiotopoulos type), late onset childhood occipital epilepsy (Gastaut type), benign epilepsy with centrotemporal spikes (BECTS), myoclonic-absence epilepsy, generalized epilepsy of unknown origin, CDKL5 mutation, bilateral polymicrogyria, Dup15q syndrome, SNAP25 mutation, febrile infection related epilepsy syndrome (FIRES), benign rolandic epilepsy infantile spasm (West syndrome), Landau-Kleffner syndrome, Dravet syndrome, Lennox-Gastaut syndrome, Aicardi syndrome, and idiopathic generalized epilepsies with variable phenotypes (juvenile absence epilepsy, juvenile myoclonic epilepsy).

In one embodiment, the epileptic disease, disorder or condition to be treated is adult epilepsy. Adult epilepsy refers to epileptic diseases, disorders or conditions as defined hereinabove, that occur after childhood (and which last or not throughout adulthood). Examples of these include, but are not limited to, tonic-clonic, clonic (with or without tonic features), absence (typical or atypical), myoclonic absence, tonic, myoclonic, massive bilateral myoclonus, negative myoclonus, eyelid myclonia (accompanied or not by absence seizures), focal epilepsies, familial and sporadic epileptic condition, lesional and non-lesional epileptic condition, myoclonic-atonic, atonic, reflex, focal sensory (with elementary sensory symptoms, such as occipital and parietal lobe seizures, or experiential sensory symptoms, such as temporo parieto occipital junction seizures, and the like), focal motor (with elementary clonic motor signs, with asymmetrical tonic motor signs or seizure, such as supplementary motor seizures, with typical automatisms, also referred to as temporal lobe automatisms, such as mesial temporal lobe seizures, with hyperkinetic automatisms, with focal negative myoclonus, with myoclonic atonic seizures and the like), inhibitory motor, gelastic seizures with hypothalamic hamartoma, hemiclonic, secondarily generalized, reflex seizures in focal epilepsy syndromes, generalized epilepsy with febrile seizures plus (GEFS+), febrile seizures plus (FS+), generalized tonic-clonic status epilepticus, clonic status epilepticus, absence status epilepticus, tonic status epilepticus, myoclonic status epilepticus, epilepsia partialis continua, aura continua, limbic status epilepticus, hemiconvulsive status epilepticus, autosomal-dominant nocturnal frontal lobe epilepsy (ADNFLE), autosomal dominant epilepsy with auditory features (ADEAF), Panayiotopoulos syndrome, Ohtahara syndrome, West syndrome, Dravet's syndrome, HH syndrome; Lennox-Gastaut syndrome, Landau-Kleffner syndrome, Rasmussen syndrome, neurocutaneous syndromes (tuberous sclerosis complex, Sturge-Weber and the like), progressive myoclonus epilepsies, epilepsy with myoclonic absences, epilepsy with myoclonic-astatic seizures, epilepsy with continuous spike-and-waves during slow-wave sleep (CSWS other than LKS), idiopathic photosensitive occipital lobe epilepsy, visual sensitive epilepsies, primary reading epilepsy, startle epilepsy, limbic epilepsies, mesial temporal lobe epilepsy with hippocampal sclerosis (MTLE with HS), mesial temporal lobe epilepsy defined by specific etiologies, other types defined by location and etiology, neocortical epilepsies, single seizures or isolated clusters of seizures, and rarely repeated seizures (oligo-epilepsy).

In one embodiment, the subject and/or at least one of its family member is/was diagnosed with an epileptic disease, disorder or condition. In one embodiment, the subject is at risk of developing an epileptic disease, disorder or condition.

In one embodiment of the invention, an onset of an epileptic disease, disorder or condition is/was diagnosed in the subject and/or in at least one of its family member. In another embodiment, no onset of an epileptic disease, disorder or condition is/was diagnosed in the subject and/or in at least one of its family member.

Methods for diagnosing an epileptic disease, disorder or condition in the subject, such as clinical tests, are well-known from the skilled artisan, and include, but are not limited to, electroencephalogram (EEG), video-EEG of the seizures, neuroimaging methods (such as computerized tomography (CT) scan, magnetic resonance imaging (MRI), functional MRI, positron emission tomography (PET), and single-photon emission computerized tomography (SPECT)), sleep tests, blood tests, neuropsychological tests, molecular assays (such as genetic testing) and the like.

In one embodiment, the subject is a mammal, preferably the subject is a human.

In one embodiment, the subject is a child (below 18 years old). In one embodiment, the subject is an adult (above 18 years old).

In one embodiment, the subject is substantially healthy. In one embodiment, the subject is/was diagnosed with or is at risk of developing an epileptic disease, disorder or condition. In one embodiment, the subject is/was diagnosed as epileptic, i.e., the subject suffers epileptic seizures. In one embodiment, an epileptic subject is defined as such when said subject has had at least one, preferably at least two or more epileptic seizures, less than at least 1, 2, 3, 4, 5 or more years apart.

In one embodiment, an onset of an epileptic disease, disorder or condition is/was diagnosed in the subject. In another embodiment, no onset of an epileptic disease, disorder or condition is/was diagnosed in the subject.

In one embodiment where the subject is a child, said subject is/was diagnosed with or is at risk of developing an infantile and juvenile epilepsy. In one embodiment where the subject is an adult, said subject is/was diagnosed with or is at risk of developing an adult epilepsy. In one embodiment where the subject is an adult, said subject is/was diagnosed with an infantile and juvenile epilepsy that lasted throughout adulthood.

In one embodiment, the subject was not previously treated with another treatment for an epileptic disease, disorder or condition (i.e., the method of the invention is a first line treatment).

In another embodiment, the subject was previously treated with at least one, two or more other treatments for an epileptic disease, disorder or condition (i.e., the method of the invention is a second, third or more line treatment). In one embodiment, the subject was previously treated with one or more other treatments an epileptic disease, disorder or condition, but was unresponsive or did not respond adequately to these treatments, i.e., the treatment induced no or low therapeutic benefit for the subject. In one embodiment, the subject is/was diagnosed with a treatment-resistant epilepsy (that may also be referred to as drug-resistant epilepsy).

In one embodiment, the subject is/was diagnosed with a brain tumor, including, but not limited to, glioma (including glioblastoma, glioblastoma multiforme, astrocytoma, pilocytic astrocytoma, diffuse astrocytoma, anaplastic astrocytoma, mixed astrocytoma I and II WHO, oligodendroglioma, anaplastic oligodendroglioma, ependymoma, and anaplastic ependymoma), craniopharyngioma, epidermoid, lymphoma, meningioma, schwannoma, pituitary adenoma, pinealoma (including pineocytoma and pineoblastoma) and medulloblastoma. In one embodiment, the brain tumor is a stage 0 tumor, a stage I tumor (also referred to as early-stage tumor), a stage II tumor, a stage III tumor or a stage IV tumor (also referred to as advanced or metastatic tumor).

In another embodiment, the subject is at risk of developing a brain tumor. Examples of risk factors for developing brain tumor include, but are not limited to, family history of cancer, genetic predisposition, and carcinogens exposure.

In one embodiment, the subject is/was diagnosed with or is at risk of developing a malformation of cortical development (MCD). In one embodiment, the subject is/was diagnosed with or is at risk of developing a MCD-related epilepsy. In one embodiment, the subject is/was diagnosed with or is at risk of developing a dysembryoplastic neuroepithelial tumour (DNET).

In one embodiment, the subject is immunosuppressed, i.e., presents an impaired immune system. In a particular embodiment, the immune system of the subject has compromised ability to fight a brain tumor.

In one embodiment, the subject suffers of nervous system dysimmune condition, with or without known antibodies targeting nervous components (such as, for example NMDA, GABA, GAD . . . ) variably associating seizures, neurological and psychiatric symptoms.

The present invention further relates to a composition for use in treating epileptic diseases, disorders or conditions in a subject in need thereof comprising, consisting or consisting essentially of probenecid or of a pharmaceutically acceptable salt thereof. In one embodiment, the present invention thus refers to probenecid alone for treating an epileptic diseases, disorders or conditions in a subject in need thereof.

In one embodiment, the composition according to the present invention does not comprise an excitatory amino acid antagonist or an excitatory amino acid receptor antagonist. Examples of excitatory amino acid antagonists or excitatory amino acid receptor antagonists include, but are not limited to, an AMPA antagonist, a strychnine insensitive glycine antagonist, or competitive NMDA antagonist. Another example of excitatory amino acid antagonist or excitatory amino acid receptor antagonist is anti-glutamatergic drugs. In particular, examples of excitatory amino acid antagonists or excitatory amino acid receptor antagonist include, but are not limited to, (2R)-amino-5-phosphonovaleric acid (AP5), barbiturates, dextromethorphan (DXM), dextrorphan, dizocilpine, ethanol, ibogaine, ifenprodil, ketamine, memantine, methoxetamine (MXE), nitrous oxide ($N_2O$), perampanel, phencyclidine (PCP), quinoxaline diones, quinoxalinic acid derivatives, indole derivatives, kynurenic acid derivatives, pyrrolidinone derivatives, D-cycloserine, its prodrugs and admixtures and isatine derivatives. Other examples of excitatory amino acid antagonists or excitatory amino acid receptor antagonist include, but are not limited to, topiramate and felbamate.

In one embodiment, the composition of the invention does not comprise an excitatory amino acid receptor antagonist selected from (2R)-amino-5-phosphonovaleric acid (AP5), barbiturates, dextromethorphan (DXM), dextrorphan, dizocilpine, ethanol, ibogaine, ifenprodil, ketamine, memantine, methoxetamine (MXE), nitrous oxide ($N_2O$), perampanel, phencyclidine (PCP), quinoxaline diones, quinoxalinic acid derivatives, indole derivatives, kynurenic acid derivatives, pyrrolidinone derivatives, D-cycloserine, its prodrugs and admixtures, isatine derivatives, 4-Bromo-6-fluorotryptophan, 4-Bromo-6-chlorotryptophan, 4-Ethyl-6-bromotryptophan, 4,6-Dibromotryptophan, 4,6-Dichlorotryptophan, 6-chloro-tryptophan, 6-fluorotryptophan, tetrazole derivatives, piperazine derivatives.

In one embodiment, the composition according to the present invention does not comprise a NMDA antagonist.

Examples of NMDA antagonists are described, for example, in GB2104078, EP420806, EP391850, U.S. Pat. Nos. 4,906,621, 4,898,854, EP302826, U.S. Pat. No. 4,746,653, EP275820, U.S. Pat. Nos. 4,705,781, 4,968,678, 4,902,687,902,695, EP418863, U.S. Pat. Nos. 4,761,405, 4,657,899, GB2157685, GB2198134, GB2201676, GB2156818, U.S. Pat. No. 4,918,064, EP364996 or EP342558, which are incorporated herein by reference.

Examples of NMDA receptor antagonists include, but are not limited to, APV, R-2-amino-5-phosphonopentanoate, methyl-5-phosphono-3-pentenoate and salts thereof, (−)-D-amino phosphonoheptanoic acid and salts thereof such as, for example, (−)2-amino-7-phospheneheptanoic acid 1,5-dibromopentane), 2-amino-6-hydroxy-4-phosphonomethyl-hex-3-enoic acid ethyl ester or a salt thereof, 2-amino-6-hydroxy-4-phosphonomethyl-hex-3-enoic acid or a salt thereof, 2,10-diamino-4-phosphonomethyl-dec-3-enoic acid or a salt thereof, 2,8-diamino-4-phosphonomethyl-oct-3-enoic acid or a salt thereof, 2-amino-6-methoxy-4-phosphonomethyl-hex-3-enoic acid ethyl ester or a salt thereof, 2-amino-6-fluoro-4-phosphonomethyl-hex-3-enoic acid ethyl ester or a salt thereof, 2-amino-6-methoxy-4-phosphonomethyl-hex-3-enoic acid or a salt thereof, 2-amino-6-benzoyloxy-4-phosphonomethyl-hex-3-enoic acid ethyl ester or a salt thereof, 2-amino-7-hydroxy-4-phosphonomethyl-hept-3-enoic acid ethyl ester or a salt thereof 2-amino-7-hydroxy-4-phosphonomethyl-hept-3-enoic acid or a salt thereof, 2-amino-6-benzyloxy-4-phosphonomethyl-hex-3-enoic acid or a salt thereof, 6-(N-acetyl-N-methyl-amino)-2-amino-4-phosphonomethyl-hex-3-enoic acid ethyl ester or a salt thereof, (1-acetylpiperidin-4-yl)-2-amino-5-phosphono-pent-3-enoic acid ethyl ester or a salt thereof, 2,10-diamino-4-phosphonomethyl-dec-3-enoic acid ethyl ester or a salt thereof, 2-amino-6-fluoro-4-phosphonomethyl-hex-3-enoic acid or a salt thereof, 2-amino-5-hydroxy-4-phosphonomethyl-pent-3-enoic acid ethyl ester or a salt thereof, 2-amino-5-hydroxy-4-phosphonomethyl-pent-3-enoic acid or a salt thereof, 2-amino-5-benzyloxy-4-phosphonomethyl-pent-3-enoic acid ethyl ester or a salt thereof, 2-amino-5-benzyloxy-4-phosphonomethyl-pent-3-enoic acid or a salt thereof, 2-amino-8-hydroxy-4-phosphonomethyl-oct-3-enoic acid ethyl ester or a salt thereof, 2-amino-8-hydroxy-4-phosphonomethyl-oct-3-enoic acid or a salt thereof, 2-amino-6-(N-methylamino)-4-phosphonomethyl-hex-3-enoic acid ethyl ester or a salt thereof, 2-amino-6-(N-methylamino)-4-phosphonomethyl-hex-3-enoic acid or a salt thereof, 2-amino-6-hydroxy-4-phosphonomethyl-hex-3-enoic acid or a salt thereof, 2-amino-6-hydroxy-4-phosphonomethyl-hex-3-enoic acid ethyl ester or a salt thereof, 2-amino-4-(piperidin-4-yl)-5-phosphono-pent-3-enoic acid ethyl ester or a salt thereof, 2-amino-4-(piperidin-4-yl)-5-phosphono-pent-3-enoic acid or a salt thereof, 5-ethoxy-2-amino-4-phosphonomethyl-pent-3-enoic acid or a salt thereof, 5-ethoxy-2-amino-4-phosphonomethyl-pent-3-enoic acid ethyl ester or a salt thereof, 2-amino-8-hydroxy-4-phosphonomethyl-oct-3-enoic acid ethyl ester or a salt thereof, 2-amino-6-hydroxy-5-hydroxymethyl-4-phosphonomethyl-hex-3-enoic acid ethyl ester or a salt thereof, 2-amino-10-hydroxy-4-phosphonomethyl-dec-3-enoic acid ethyl ester or a salt thereof, cis ethyl 4-[1-(3-phosphonoprop-1-enyl)]-piperidine-2-carboxylate or salt thereof, trans 4-[1-(3-phosphonoprop-1-enyl)]-piperidine-2-carboxylic acid or slat thereof, trans-4-[1-(3-phosphonoprop-2-enyl)]-piperidine-2-carboxylic acid or salt thereof, cis 4-[1-(3-phosphonoprop-1-enyl)]-piperidine-2-carboxylic acid or salt thereof, cis 4-[1-(3-phosphonoprop-2-enyl)]-piperidine-2-carboxylic acid or salt thereof, E-2-amino-4-phosphonomethyl-hept-3-ene-1,7-diacid diethyl ester or a salt thereof, E-2-amino-4-phosphonomethyl-hept-3-en-1,7-diacid or a salt thereof, E-2-amino-4-phosphonomethyl-hept-3-ene-1,7-dibenzyl ester or a salt thereof, cis-4-phosphonomethyl-2-piperidinecarboxylic acid or salt thereof, cis-4-(3-phosphonopropyl)-2-piperidinecarboxylic acid or salt thereof, cis-4-phosphonomethyl-2-piperidinecarboxylic acid ethyl ester or salt thereof, 4-[1-(3-phosphonoprop-1-enyl)] piperidine-2-carboxylic acid or salt thereof, cis-5-methyl-4-phosphonomethyl-2-piperidinecarboxylic acid or salt thereof, (−)-cis-4-phosphonomethyl-2-piperidinecarboxylic acid or salt thereof, cis-4-phosphonomethyl-2-piperidinecarboxylic acid methyl ester or salt thereof, E-2-amino-4-methyl-5-phosphono-3-pentenoate or salt thereof, E-2-amino-4-methyl-5-phosphono-3-pentenoic acid ethyl ester, E-2-amino-4-methyl-5-phosphono-3-pentenoic acid or salt thereof, E-2-amino-4-methyl-5-phosphono-3-pentenoic acid or salt thereof, E-2-amino-4-methyl-5-phosphono-3-pentenoic acid methyl ester or salt thereof, E-2-amino-4-methyl-5-phosphono-3n-propylpenic acid or salt thereof, N-butyl E-2-amino-4-methyl-5-phosphono-3-pentenoate or salt thereof, E-2-amino-4-methyl-5-phosphono-3-pentenoic acid iso butyl ester or salt thereof, E-2-amino-4-methyl-5-phosphono-3-pentenoic acid n-hexyl ester or salt thereof, (2R)-E-2-amino-4-methyl-5-phosphono-3-pentenoic acid or salt thereof, (2R)-E-2-amino-4-methyl-5-phosphono-3-pentenoic acid or salt thereof, ethyl (2R)-E-2-amino-4-methyl-5-phosphono-3-pentenoate or salt thereof, (2R)-E-2-amino-4-methyl-5-phosphono-3-pentenoic acid ethyl ester or salt thereof, 4-(alpha-phosphonoacetamido)-piperidine-2-carboxylic acid or salt thereof, 4-(2-phosphonoethylamino) piperidine-2-carboxylic acid or salt thereof, 4-[1-(3-phosphonoprop-2-enyl)]-piperidine-2-carboxylic acid and salt thereof, 4-[1-(3-phosphonoprop-1-enyl)]-piperidine-2-carboxylic acid and salt thereof, trans 3-[1-(4-phosphonobut-3-enyl)]-pyrrolidine-2-carboxylic acid and salt thereof, trans 3-[1-(4-phosphonobut-2-enyl)]-pyrrolidine-2-carboxylic acid and salt thereof, cis-4-[1-(3-phosphonoprop-2-enyl)]-piperidine-2-carboxylic acid and salt thereof, trans 4-[1-(3-phosphonoprop-2-enyl)]-piperidine-2-carboxylic acid and salt thereof, cis 4-[1-(3-phosphonoprop-1-enyl)]-piperidine-2-carboxylic acid and salt thereof, trans 4-[1-(3-phosphonoprop-1-enyl)]-piperidine-2-carboxylic acid and salt thereof, cis 3-[1-(4-phosphonobut-3-enyl)]-pyrrolidine-2-carboxylic acid and salt thereof, 4-(phosphono substituted lower alkyl or lower alkenyl)piperazine-2-carboxylic acids and salts, esters and amides thereof, 4-[(1(2)H-tetrazol-5-yl)methyl]-2-piperidinecarboxylic acid or a diastereomer or stereospecific isomer or salt thereof, cis-(−)-4[1(2)H-tetrazol-5-yl)methyl]-2-piperidinecarboxylic acid or salt thereof, 4-[2-(1(2)H-tetrazol-5-yl)ethyl]-2-piperidinecarboxylic acid or a diastereomer or stereospecific isomer or salt thereof, 4-[3-(1(2)H-tetrazol-5-yl)propyl]-2-piperidinecarboxylic acid or a diastereomer or stereospecific isomer or salt thereof, 4-[1(2)H tetrazol-5-yl)methylidene]-2-piperidinecarboxylic acid or a diastereomer or stereospecific isomer or salt thereof, 4-[3-(1(2)H-tetrazol-5-yl)propyl]-2-piperazinecarboxylic acid and salt thereof, 4-[2-(1(2)H-tetrazol-5-yl)ethyl]-2-piperazinecarboxylic acid and salt thereof, N-benzyloxycarbonyl-D-aspartic acid, N-benzyloxycarbonyl-3-methyl-D,L-aspartic acid, N-benzoylcarbonyl-D-2-aminoadipic acid, R-5-oxo-4-acetic-3-oxazolidinecarboxylic acid, 3-(phenylmethyl) ester, S-5-oxo-4-acetic-3-oxazolidinecarboxylic acid, 3-(phenylmethyl) ester, R,S-5-oxo-4-(α-methyl acetic acid)-3-oxazolidine carboxylic acid, 3-phenyl(methyl) ester, R-5-oxo-4-butyric-3-oxazolidinecarboxylic acid, 3-(phenylmethyl) ester, R-5-oxo-4-(acetyl chloride)-3-oxazolidinecarboxylic acid, 3-(phenylmethyl) ester, S-5-oxo-4-(acetyl chloride)-3-oxazolidine carboxylic acid, 3-(phenylmethyl) ester, R,S-5-oxo-4-(α-methyl-acetyl chloride)-3-oxazolidine carboxylic acid, 3-(phenylmethyl) ester, R-5-oxo-4-(butryl chloride)-3-oxazolidine carboxylic acid, 3-(phenylmethyl) ester, R-4-[3-(diethoxyphosphinyl)-2-oxopropyl]-5-oxo-3-oxazolidine carboxylic acid, 3-(phenylmethyl) ester, S-4-[3-(diethyloxyphosphinyl)-2-oxopropyl)-5-oxo-3-oxazolidine carboxylic acid, 3-(phenylmethyl) ester, 4-[3-(diethoxyphosphinyl)-1-methyl-2-oxopropyl]-5-oxo-3-diethyl phosphonate)-3-oxazolidine carboxylic acid, 3-(phenyl methyl) ester, 4-[3-(diethoxyphosphinyl)-1,3-dimethyl-2-oxopropyl]-5-oxo-3-oxazolidinecarboxylic acid, 3-(phenylmethyl) ester, R-4-[3-(diethoxyphosphinyl-3-methyl-2-oxopropyl]-5-oxo-3-oxazolidine carboxylic acid, 3-(phenylmethyl) ester, R-4-[5-(Diethoxyphosphinyl)-4-oxopentyl]-5-oxo-3-oxazolidine carboxylic acid, 3-(phenyl methyl) ester, R-4-oxo-5-phosphononorvaline, S-4-oxo-5-phosphononorvaline, 3,4-dimethyl-4-oxo-5-phosphononorvaline, 3-methyl-4-oxo-5-phosphononorvaline, R-5-methyl-4-oxo-5-phosphononorvaline, R-2-Amino-6-oxo-7-phosphonoheptanoic acid, 4-(2-oxo-3-phosphonopropyl)-2-piperazinecarboxylic acid, 2-methyl-4-oxo-5-phosphononorvaline, 5-(Hydroxymethoxyphosphinyl)-4-oxonorvaline, 4-(Hydroxyimino)-5-phosphononorvaline, 4-(Methoxyimino)-5-phosphononorvaline, 4-[(phenylmethoxy)imino]-5-phosphononorvaline, 4-[(2'-phenylethoxy)imino]-5-phosphononorvaline, 4-(benzylhydrazino)-5-phosphononorvaline, R-4-oxo-5-phosphononorvaline methyl ester, R-4-oxo-5-phosphononorvaline ethyl ester, 3-{2-phosphonoethylcyclohexyl}-2-aminopropanoic acid, 4-[2-phosphonomethylcyclohexyl]-2-aminobutanoic acid, 4-[2-phosphonomethylphenyl]-2-amino-butanoic acid, ethyl 3-[2-(2-diethylphosphonoethyl)-phenyl]-2-acetamido-2-carbethoxypropanoate, 3-[2-(2-phosphonoethyl)-phenyl]-2-aminopropanoic acid, 3-[2-phosphonomethylphenyl]-2-amino-propanoic acid, 3-[2-(3-phosphonopropyl)-phenyl]-2-aminopropanoic acid, 5-[2-phosphonomethylphenyl]-2-amino-pentanoic acid, 3-((+/−)-2-carboxypiperazin-4-yl) propyl-1-phosphonic acid, α-amino-α-(3-alkylphenyl) alkyl-ethanoic acid, an ester thereof or an amide or salt thereof, (+/−)-α-amino-3(4'-chloro-5-phosphonomethyl-[1.1'-biphenyl]-3-yl) propanoic acid or a salt thereof, (+/−)-α-amino-3-(3-phosphonomethyl)phenyl-propanoic acid or a salt thereof, (+/−)-α-amino-3-(5-phosphonomethyl-[1.1'biphenyl]-3-yl) propanoic acid or a salt thereof, (+/−)-α-amino-3-(5-octyloxy-3-phosphonomethyl)phenyl-propanoic acid or a salt thereof, (+/−)-α-amino-3-(5-diethoxyphosphinyl)methyl-[1.1']-3-yl) propanoic acid ethyl ester or a salt thereof, (+/−)-α-amino-3-(5-phosphonomethyl-[1.1'-biphenyl]-3-yl) propanoic acid ethyl ester or a salt thereof, (+/−)-α-amino-3-(4'-chloro-5-(diethoxyphosphinyl) methyl-[1.1'-biphenyl]-3-yl)propanoic acid amide or a salt thereof, (+/−)-α-amino-3-(4'-chloro-5-phosphonomethyl-[1.1'-biphenyl]-3-yl) propanoic acid amide or a salt thereof, (+/−)-α-palmitoylamino-3-(5-phosphonomethyl-[1.1'-biphenyl]-3-yl) propanoic acid or a salt thereof, (+/−)-α-amino-3-(4'-chloro 5 (diethoxyphosphinyl) methyl-[1.1'-biphenyl]-3-yl) propanoic acid methyl ester or a salt thereof, (+/−)-α-amino-3-(4'-chloro-5-phosphonomethyl-[1.1'-biphenyl]-3-yl) propanoic acid methyl ester or a salt thereof, (+/−)-α-amino-3-(4'-chloro-5-(diethoxyphosphinyl)methyl-[1.1'-biphenyl]-3-yl) propanoic acid or a salt thereof, (+/−)-α-tert.butyloxycarbonylamino-3-(4'-chloro-5-(diethoxyphosphinyl)methyl-[1.1'-biphenyl]-3-yl) propanoic acid or a salt thereof, (+/−)-α-tert.butyloxycarbonylamino-3 (4'-chloro-5-(diethoxyphosphinyl)methyl-[1.1'-biphenyl]-3-yl) propanoic acid cinnamyl ester, (+/−)-α-amino-3-(4'-chloro-5-(diethoxyphosphinyl)methyl-[1.1'-biphenyl]-3-yl) propanoic acid cinnamyl ester or a salt thereof, (+/−)-α-amino-3-(4'chloro-5phosphonomethyl-[1.1'-biphenyl]-3-yl) propanoic acid cinnamyl ester or a salt thereof, (+/−)-α-amino-3-(5-cyclic-2,2-dimethylpropylene phosphinyl)methyl[1.1'-biphenyl]3-yl) propanoic acid ethyl ester or a salt thereof, (+/−)-α-amino-3 (4'-tert.butyl-5-phosphonomethyl-[1.1'-biphenyl]-3-yl) propanoic acid or a salt thereof, (+/−)-α-amino-3-(4-'phenyl-5-phosphonomethyl-[1.1'-biphenyl]-3-yl)propanoic acid or a salt thereof, (+/−)-α-amino-3-(4-chloro-5-phosphonomethyl-[1.1'-biphenyl]-3-yl) propanoic acid benzoylmethyl ester or a salt thereof, (+/−)-α-amino-3-(5-phosphonomethyl-[1.1'-biphenyl]-3-yl) propanoic acid methyl ester or a salt thereof, (+/−)-α-acetylamino-3(5-phosphononiothyl-[1.1'-biphenyl]-3-yl) propanoic acid or a salt thereof, (+/−)-α-amino-3-(3-amino-5-phosphonomethyl-[1.1'-biphenyl]-3-yl) propanoic acid or a salt thereof, (+)-α-amino-3-(5-(diethoxyphosphinyl)methyl-[1.1'-biphenyl]-3-yl)propanoic acid ethyl ester or a salt thereof, (+)-α-amino-3-(5-phosphonomethyl-[1.1'-biphenyl]-3-yl)propanoic acid ethyl ester or a salt thereof, (+)-α-amino-3-(5-phosphonomethyl-[1.1'-biphenyl]-3-yl) propanoic acid or a salt thereof, (−)-α-amino-3-(5-(diethoxyphosphinyl)methyl-[1.1'-biphenyl]-3-yl)propanoic acid ethyl ester or a salt thereof, (−)-α-amino-3-(5-phosphonomethyl-[1.1'-biphenyl]-3-yl)propanoic acid ethyl ester or a salt thereof, (−)-α-amino-3-(5-phosphonomethyl-[1.1'-biphenyl]-3-yl) propanoic acid or a salt thereof, [R-(E)]-4-(3-phosphono-2-propenyl)-2-piperazinecarboxylic acid or salt thereof, (+)-S-(3-phosphonopropyl)-D-cysteine or a salt thereof, S-(3-phosphonopropyl)-D,L-cysteine or a salt thereof, S-(2-phosphonoethyl)-D,L-homocysteine or a salt thereof, N-benzyloxycarbonyl-S-(3-phosphonopropyl)-D,L-cysteine or a salt thereof, S-[3-[(dodecyloxy)hydroxyphosphinyl]propyl]-D,L cysteine or a salt thereof, (−)-N-(carboxymethyl)-N-phenyl-D-glutamine or a salt thereof, (+)-N-(carboxymethyl)-N-phenyl-L-glutamine or a salt thereof, (−)-N-(carboxymethyl)-N-(4-chlorophenyl)-D-glutamine or a salt thereof, (−)-3-((3-phosphonopropyl)sulfinyl]-D-alanine or a salt thereof, (+)-3-((3-phosphonopropyl)sulfonyl-D-alanine or a salt thereof, 4-(phosphonomethyl)phenylglycine, 4-(Ethyl phosphonomethyl)phenylglycine, 2,5-dimethyl-4-(phosphonomethyl)phenylglycine hydrochloride, 3-carboxy-5-phosphono-1,2,3,4-tetrahydroisoquinoline hydrochloride, 3-carboxy-5-phosphono-1,2,3,4-tetrahydroisoquinoline, 3-carboxy-5 phosphono-1,2,3,4,5,8-hexahydroisoquinoline, 3-carboxy-5-phosphono-1,2,3,4,5,6,7,8-octahydroisoquinoline, 3-carboxy-5-phosphono-6-methyl-1,2,3,4-tetrahydroisoquinoline, 3-carboxy-5-phosphono 7 methyl-1,2,3,4-tetrahydroisoquinoline, 3-carboxy-5-phosphono-8-methyl-1,2,3,4-tetrahydroisoquinoline, 3-carboxy-5-phosphono-6-chloro-1,2,3,4-tetrahydroisoquinoline, 3-carboxy-5-phosphono-7-chloro-1,2,3,4-tetrahydroisoquinoline, 3-carboxy-5-phosphono-8-chloro-1,2,3,4-tetrahydroisoquinoline, (D)-3-carboxy-5-phosphono-1,2,3,4-tetrahydroisoquinoline, (L)-3-carboxy-5-phosphono-1,2,3,4-tetrahydroisoquinoline, 5-phosphono-3-

(ethoxycarbonyl)-1,2,3,4-tetrahydroisoquinoline, 5-(ethyl phosphono)-3-carboxy-1,2,3,4-tetrahydroisoquinoline, 3-cis-carboxy-5-cis-phosphono-cis-2-azadecalin, 3-cis-carboxy-5-trans-phosphono-cis-2-azadecalin, 3-trans-carboxy-5-trans-phosphono-cis-2-azadecalin, 3-trans-carboxy-5-cis-phosphono-cis-2-azadecalin, 3-cis-carboxy-5-cis-phosphono-trans-2-azadecalin, 3-cis-carboxy-5-trans-phosphono-trans-2-azadecalin, 3-trans-carboxy-5-trans-phosphono-trans-2-azadecalin, 3-trans-carboxy-5-cis-phosphono-trans-2-azadecalin, 3-carboxy-5-(phosphonomethyl)-1,2,3,4-tetrahydroisoquinoline, 3-carboxy-5-(2-phosphonoethyl)-1,2,3,4-tetrahydroisoquinoline, 3-carboxy-5-(2-phosphonoethenyl)-1,2,3,4-tetrahydroisoquinoline, D,L-3-carboxy-5-phosphono-1,2,3,4-tetrahydroisoquinoline, D-3-carboxy-5-phosphono-1,2,3,4-tetrahydroisoquinoline, (+)-3-carboxy-5-phosphono-1,2,3,4-tetrahydroisoquinoline, 5-phosphono-3-(ethoxycarbonyl)-1,2,3,4-tetrahydroisoquinoline, 3-carboxy-5-phosphono-6-methyl-1,2,3,4-tetrahydroisoquinoline, 3-carboxy-5-(phosphonomethyl)-1,2,3,4-tetrahydroisoquinoline, 3-carboxy-5-phosphono-1,2,3,4,5,8-hexahydroisoquinoline, 3-carboxy-5-phosphono-1,2,3,4,5,6,7,8-octahydroisoquinoline, 3-carboxy-5-phosphono-2-azadecalin, 2R,4S,5R-2-amino-4,5-methylene-adipic acid, 2R,4R,5R-2-amino-4,5-methylene-adipic acid, 2R,4S,5S-2-amino-4,5-methylene-adipic acid, 2R,4R,5S-2-amino-4,5-methylene-adipic acid, 2S,4S,5R-2-amino-4,5-methylene-adipic acid, 2S,4R,5R-2-amino-4,5-methylene-adipic acid, 2S,4S,5S-2-amino-4,5-methylene-adipic acid, 2S,4R,5S-2-amino-4,5-methylene-adipic acid, 2R,4S,5R-2-amino-4,5-methylene-adipic acid diethyl ester, 2R,4R,5R-2-amino-4,5-methylene-adipic acid diethyl ester, 2R,4S,5S-2-amino-4,5-methylene-adipic acid diethyl ester, 2R,4R,5S-2-amino-4,5-methylene-adipic acid diethyl ester, 2S,4S,5R-2-amino-4,5-methylene-adipic acid diethyl ester, 2S,4R,5R-2-amino-4,5-methylene-adipic acid diethyl ester, 2S,4S,5S-2-amino-4,5-methylene-adipic acid diethyl ester, 2S,4R,5S-2-amino-4,5-methylene-adipic acid diethyl ester, 2R,4S,5R-2-amino-4,5-methylene-adipic acid-1-methyl-6-ethyl ester, 2R,4R,5R-2-amino-4,5-methylene-adipic acid-1-methyl-6-ethyl ester, 2R,4S,5S-2-amino-4,5-methylene-adipic acid-1-methyl-6-ethyl ester, 2R,4R,5S-2-amino-4,5-methylene-adipic acid-1-methyl-6-ethyl ester, 2S,4S,5R-2-amino-4,5-methylene-adipic acid-1-methyl-6-ethyl ester, 2S,4R,5R-2-amino-4,5-methylene-adipic acid-1-methyl-6-ethyl ester, 2S,4S,5S-2-amino-4,5-methylene-adipic acid-1-methyl-6-ethyl ester, 2S,4R,5S-2-amino-4,5-methylene-adipic acid-1-methyl-6-ethyl ester, 2R,4S,5R-2-acetylamino-4,5-methylene-adipic acid, 2R,4R,5R-2-acetylamino-4,5-methylene-adipic acid, 2R,4S,5S-2-acetylamino-4,5-methylene-adipic acid, 2R,4R,5S-2-acetylamino-4,5-methylene-adipic acid, 2S,4S,5R-2-acetylamino-4,5-methylene-adipic acid, 2S,4R,5R-2-acetylamino-4,5-methylene-adipic acid, 2S,4S,5S-2-acetylamino-4,5-methylene-adipic acid, 2S,4R,5S-2-acetylamino-4,5-methylene-adipic acid, 2R,4S,5R-2-acetylamino-4,5-methylene-adipic acid diethyl ester, 2R,4R,5R-2-acetylamino-4,5-methylene-adipic acid diethyl ester, 2R,4S,5S-2-acetylamino-4,5-methylene-adipic acid diethyl ester, 2R,4R,5S-2-acetylamine-4,5-methylene-adipic acid diethyl ester, 2S,4S,5R-2-acetylamino-4,5-methylene-adipic acid diethyl ester, 2S,4R,5R-2-acetylamino-4,5-methylene-adipic acid diethyl ester, 2S,4S,5S-2-acetylamino-4,5-methylene-adipic acid diethyl ester, 2S,4R,5S-2-acetylamino-4,5-methylene-adipic acid diethyl ester, 2R,4S,5R-2-benzyloxycarbonylamino-4,5-methylene-adipic acid diethyl ester, 2R,4R,5R-2-benzyloxycarbonylamino-4,5-methylene-adipic acid diethyl ester, 2R,4S,5S-2-benzyloxycarbonylamino-4,5-methylene-adipic acid diethyl ester, 2R,4R,5S-2-benzyloxycarbonylamino-4,5-methylene-adipic acid diethyl ester, 2S,4S,5R-2-benzyloxycarbonylamino-4,5-methylene-adipic acid diethyl ester, 2S,4R,5R-2-benzyloxycarbonylamino-4,5-methylene-adipic acid diethyl ester, 2S,4S,5S-2-benzyloxycarbonylamino-4,5-methylene-adipic acid diethyl ester, 2S,4R,5S-2-benzyloxycarbonylamino-4,5-methylene-adipic acid diethyl ester, 2R,4S,5R-2-benzyloxycarbonylamino-4,5-methylene-adipic acid-1-methyl-6-ethyl ester, 2R,4R,5R-2-benzyloxycarbonylamino-4,5-methylene-adipic acid-1-methyl-6-ethyl ester, 2R,4S,5S-2-benzyloxycarbonylamino-4,5-methylene-adipic acid-1-methyl-6-ethyl ester, 2R,4R,5S-2-benzyloxycarbonylamino-4,5-methylene-adipic acid-1-methyl-6-ethyl ester, 2S,4S,5R-2-benzyloxycarbonylamino-4,5-methylene-adipic acid-1-methyl-6-ethyl ester, 2S,4R,5R-2-benzyloxycarbonylamino-4,5-methylene-adipic acid-1-methyl-6-ethyl ester, 2S,4S,5S-2-benzyloxycarbonylamino-4,5-methylene-adipic acid-1-methyl-6-ethyl ester, and 2S,4R,5S-2-benzyloxycarbonylamino-4,5-methylene-adipic acid-1-methyl-6-ethyl ester. In one embodiment, the composition according to the present invention does not comprise kynurenine or kynurenine derivatives or kynurenic acid derivatives. Examples of kynurenic acid derivatives are described, for example, in EP386839 or EP303387, which are incorporated herein by reference. Examples of kynurenine derivatives include, but are not limited to, 4,6-Dichloro-kynurenine, 4-fluoro-6-bromo-kynurenine, 4-chloro-6-bromo-kynurenine, 4,6-Dibromo-kynurenine, 6-Ethyl-4-bromokynurenine, 4-chloro-kynurenine, 4-fluoro-kynurenine, 6-Bromo-4-chlorokynurenine and 6-Bromo-4-bromokynurenine.

In one embodiment, the composition of the invention does not comprise a quinaxoline dione. Examples of quinaxoline diones are described, for example, in EP377112, EP374534, EP348872, EP315959, EP260467, U.S. Pat. Nos. 4,889,855 or 4,812,458, which are incorporated herein by reference. Examples of quinaxoline diones include, but are not limited to, 7-cyano-1-hydroxy-6-trifluoromethylquinoxaline-2,3 (1H,4H)-dione, 7-chloro-1-hydroxy-6-trifluoromethylquinoxaline-2,3(1H,4H)-dione, 1-hydroxy-7-sulfamoyl-6-trifluoromethylquinoxaline2,3(1H,4H)-dione, and 7-acetyl-6-cyano-1-hydroxyquinoxaline-2,3(1H,4)-dione, 4-hydroxybenzo quinoxaline-2,3(1H,4H)-dione, 6-cyano-4-hydroxybenzo[f]quinoxaline-2,3(1H,4H)-dione, 4-hydroxypyrido[3,2-f]quinoxaline-2,3(1H,4H)-dione, 7,8,9,10-tetrahydro-4-hydroxybenzo quinoxaline-2,3(1H,4H)-dione, 7,8-dihydroxy-1-methyl-4-nitro-1H-1,2,3-triazolo[4,5-f] quinoxaline, 7,8-dihydroxy-3-methyl-4-nitro-3H-1,2,3-triazolo[4,5-f]quinoxaline, 8-carboxy-2,3-dihydroxythieno [3,2-f]quinoxaline, 7,8-dihydroxy-4-nitro-1,2,5-thiadiazolo (3,4-f)quinoxaline, 1-cyclohexyl-6-nitroquinoxaline-2,3 (1H,4H)-dione, 1-benzyl-6-nitroquinoxaline-2,3(1H,4H)-dione, 4-methylbenzo[f]quinoxaline-2,3(1H,4H)-dione, 1-cyclohexyl-7-chloroquinoxaline-2,3(1H,4H)-dione, 6-cyano-7-nitro-2,3-dihydroxyquinoxaline, 6-chloro-7-cyano-2,3-dihydroxyquinoxaline, 6-trifluoromethyl-7-cyano-2,3-dihydroxyquinoxaline, 2,3-dihydroxy-6,7-dinitrobenzo(f)quinoxaline, 2,3-dihydroxy-6,10-dinitrobenzo(f) quinoxaline, 6-bromo-2,3-dihydroxy-10-nitrobenzo(f) quinoxaline.

In one embodiment, the composition according to the present invention does not comprise a quinoxaline dione AMPA antagonist, such as, e.g., ACEA-1011 (5-chloro-7-(trifluoromethyl)quinoxaline-2,3-diol), AMP397 ((({[(7-nitro-2,3-dioxo-1,2,3,4-tetrahydro-5-quinoxalinyl)methyl] amino}methyl)phosphonic acid; Becampanel), CNQX (7-nitro-2,3-dioxo-1,4-dihydroquinoxaline-6-carbonitrile), DNQX (6,7-dinitroquinoxaline-2,3-dione), MPQX ({[7-(4-morpholinyl)-2,3-dioxo-6-(trifluoromethyl)-3,4-dihydro-1(2H)-quinoxalinyl]methyl}phosphonic acid; Fanapanel), ACEA-1021 (6,7-dichloro-1,4-dihydro-5-nitro-2,3-quinoxalinedione, Licostinel), NBQX (2,3-dioxo-6-nitro-1,2,3,4-tetrahydrobenzo[f]quinoxaline-7-sulfonamide), PNQX (1,4,7,8,9,10-hexahydro-9-methyl-6-nitropyrido[3,4-f]quinoxaline-2,3-dione), YM90K (6-(1H-imidazol-1-yl)-7-nitro-2,3(1H,4H)-quinoxalinedione hydrochloride), YM872 ((2,3-dioxo-7-(1H-imidazol-1-yl)-6-nitro-1,2,3,4-tetrahydro-1-quinoxalinyl)-acetic acid monohydrate; Zonampanel) and derivatives thereof.

In one embodiment, the composition of the invention does not comprise a quinoxalinic acid derivative.

In one embodiment, the composition of the invention does not comprise an indole derivative. Examples of indole derivatives are described, for example, in U.S. Pat. No. 4,960,786 or EP396124, which are incorporated herein by reference. Examples of indole derivatives include, but are not limited to, 3-(2-carboxy-6-methoxyindol-3-yl)propionic acid, 3-(2-carboxy-6-chloroindol-3-yl)propionic acid, 3-(2-carboxy-4,6-dichloroindol-3-yl)propionic acid, 3-(2-carboxy-6-trifluoromethoxyindol-3-yl)propionic acid, 3-(2-carboxy-4-trifluoromethylindol-3-yl)propionic acid, 3-(2-carboxy-6-trifluoromethylindol-3-yl)propionic acid, 3-(2-carboxy-4-fluoroindol-3-yl)propionic acid, 3-(2-carboxy-4-nitroindol-3-yl)propionic acid, 3-(2-carboxy-6-nitroindol-3-yl)propionic acid, ethyl 3-(2-carboxyethyl-4,6-dichloroindol-3-yl) propionate, benzyl 3-(2-carboxybenzyl-4,6-dichloroindol-3-yl) propionate, 3-(2-Carboxamide-4,6-dichloroindol-3-yl)propionamide, 2-(2-carboxy-6-chloroindol-3-yl)acetic acid, 4-(2-carboxy-6-chloroindol-3-yl)butyric acid, 5-(2-carboxy-6-chloroindol-3-yl)pentanoic acid, 3-(2-carboxy-4,6-dichloro-1-methylindol-3-yl), 3-(2-carboxy-6-methoxyindol-3yl)propionic acid, 3-(2-carboxy-6-chloroindol-3 yl)propionic acid, 2-carboxy-3-indoleacetic acid, 2-carboxy-1-methyl-3-indoleacetic acid, 2-carboxy-5-chloro-3-indoleacetic acid, 5-bromo-2-carboxy-3-indoleacetic acid, 2-carboxy-5-fluoro-3-indoleacetic acid, ethyl 2-carboxy-6-chloro-3-indoleacetate, 2-carboxy-6-chloro-3-indoleacetamide, 2-carboxy-6-chloro-3-indoleacetic acid 3-ethylamide, ethyl 6-chloro-3-(2-chloroethyl)-2-indolecarboxylate, 2-carboxy-6-chloro-3-indoleacetic acid and 2-carboxy-6-chloro-3-indoleacetic acid.

In one embodiment, the composition of the invention does not comprise a pyrrolidinone derivative. Examples of pyrrolidinone derivatives are described, for example, in U.S. Pat. Nos. 4,925,867, 4,863,953 or GB2231048, which are incorporated herein by reference. Examples of pyrrolidinone derivative include, but are not limited to, cis-3-amino-1-hydroxy-4-methylpyrrolidin-2-one or salt thereof, (3R,4R)-3-amino-1-hydroxy-4-methylpyrrolidin-2-one or salt thereof, cis-3-amino-1-hydroxy-4-ethylpyrrolidin-2-one or salt thereof, (3R)-3-amino-1-hydroxypyrrolidin-2-one, (3R)-3-amino-1-hydroxypyrrolidin-2-one, (3R)-amino-1-hydroxypyrrolidin-2-one, 2,6-diaza-6-hydroxy-7-oxobicyclo-[3.2.1]-octane and salt thereof and 2,6-diaza-6-hydroxy-8-endo-methyl-7-oxobicyclo-[3.2.1]-octane and salt thereof.

In one embodiment, the composition of the invention does not comprise D-cycloserine, a prodrug thereof or an admixture thereof. Examples of D-cycloserine, prodrugs thereof or admixtures thereof are described, for example, in EP387867, EP378134 or U.S. Pat. No. 4,904,681, which are incorporated herein by reference. Examples of D-cycloserines include, but are not limited to, 4-amino-3-isoxazolidone, D-4-amino-3-isoxazolidone or salts thereof.

In one embodiment, the composition of the invention does not comprise an isatine derivative.

In one embodiment, the composition of the invention does not comprise a bicyclic derivative. Examples of bicyclic derivatives are described, for example, in U.S. Pat. No. 4,902,695, which is incorporated herein by reference. Examples of bicyclic derivatives include, but are not limited to decahydro-6-5-[1(2)H-tetrazol-5-ylmethyl]-3-isoquinolinecarboxylic acid or salts thereof, 3-carboxydecahydro-6-isoquinolineacetic acid or salts thereof, decahydro-6-(phosphomethyl)-3-isoquinolinecarboxylic acid or salts thereof, decahydro-6-(phosphomethyl)-1-isoqunolinecarboxylic acid hydrochloride hemihydrate, decahydro-6-tetrazol-5-yl-methyl)-1-isoquinolinecarboxylic acid, decahydro-6-(phosphonomethyl)-3-isoquinololine-carboxylic acid ethyl ester, decahydro-6-(phosphonomethyl)-3-isoquinoline carboxylic acid butyl ester, decahydro-6-5.

In one embodiment, the composition according to the present invention does not comprise eslicarbazepine, eslicarbazepine acetate or derivatives thereof.

In one embodiment, the composition according to the present invention does not comprise a compound of Formula (II) or a salt thereof:

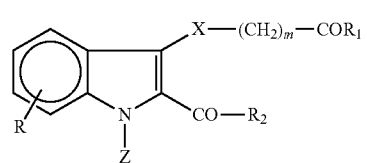

wherein X is a linear $C_{1-4}$ alkylene or S; m is an integer from 1-4; Z is hydrogen, $C_{1-4}$ alkyl, phenyl, substituted phenyl or alkylphenyl substituent in which the phenyl ring may be optionally substituted; R is hydrogen, halogen, $C_{1-4}$ alkyl, $C_{1-4}$ alkoxy, $CF_3$, $OCF_3$, OH, $NO_2$ or CN; $R_1$ and $R_2$ are each independently —OH, —$OR_3$, —$NR_4R_5$, —$OCH_2OR_3$ or —O—$(CH_2)_n$—$NR_6R_7$, in which n is an integer from 1-4; $R_3$ is $C_{1-4}$ alkyl, phenyl, substituted phenyl or alkylphenyl substituent in which the phenyl ring may be optionally substituted; $R_4$ and $R_5$ are each independently hydrogen or $C_{1-4}$ alkyl; $R_6$ and $R_7$ are each independently hydrogen or $C_{1-4}$ alkyl, or $R_6$ and $R_7$ together with the adjacent nitrogen atom form a piperidino, morpholino or pyrrolidino group with the proviso that if X is a $C_{1-4}$ alkylene, then m is 0.

In one embodiment, the composition according to the present invention does not comprise a compound of Formula (III) or a salt thereof:

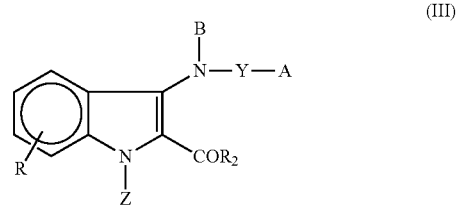

wherein R, Z, and $R_2$ are defined as above in Formula (II); B is hydrogen, $C_{1-4}$ alkyl, optionally substituted alkylphenyl or —CH$_2$—COR$_2$; Y is SO$_2$ or CO; and A is phenyl, substituted phenyl or C(O)D in which D is defined as R$_2$ in Formula (II).

In one embodiment, the composition according to the present invention does not comprise a compound of formula (IV) or a salt thereof:

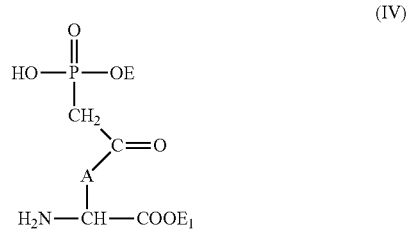

wherein E is hydrogen, C$_{1-4}$ alkyl or —CF$_3$; A is a methylene or a trimethylene bridging group; and E$_1$ is hydrogen, C$_{1-4}$ alkyl, cycloalkyl, trialkylamino, alkylphenyl, phenyl, or substituted phenyl.

In one embodiment, the composition according to the present invention does not comprise a compound of formula (V) or a salt thereof:

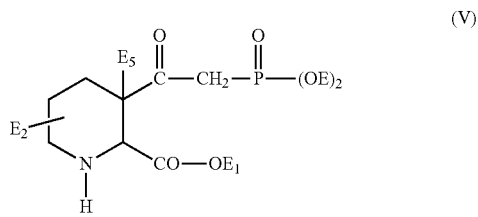

wherein E and E$_1$ are defined as above in Formula (IV), E$_2$ is hydrogen, C$_{1-4}$ alkyl, phenyl, alkylphenyl or cyclohexylmethyl; and E$_5$ is hydrogen, linear C$_{1-4}$ alkyl or alkylphenyl.

In one embodiment, the composition according to the present invention does not comprise a compound of formula (VI) or a salt thereof:

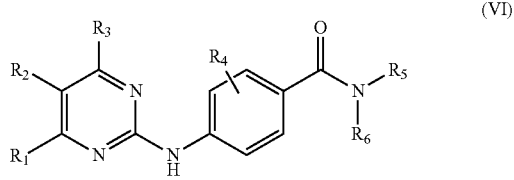

wherein R$_1$ is aryl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl or quinazolinyl, each optionally substituted with one to four substituents independently selected from R$_7$; R$_2$ and R$_3$ are the same or different and are independently hydrogen or lower alkyl; R$_4$ represents one to four optional substituents, wherein each substituent is the same or different and independently selected from halogen, hydroxy, lower alkyl or lower alkoxy; R$_5$ and R$_6$ are the same or different and independently —(CH$_2$)$_a$C(=O)R$_9$, —(CH$_2$)$_a$C(=O)OR$_9$, —(CH$_2$)$_a$C(=O)NR$_9$R$_{10}$, —(CH$_2$)$_a$C(=O)NR$_9$(CH$_2$)$_b$C(=O)R$_{10}$, —(CH$_2$)$_a$NR$_9$C(=O)R$_{10}$, —(CH$_2$)$_a$NR C(=O)NR$_9$R$_{10}$, —(CH$_2$)$_a$OR$_9$, —(CH$_2$)$_a$SO$_c$R$_9$, or —(CH$_2$)$_a$SO$_2$NR$_9$R$_{10}$; or R$_5$ and R$_6$ taken together with the nitrogen atom to which they are attached form a heterocycle or substituted heterocycle; R$_7$ is at each occurrence independently halogen, hydroxy, cyano, nitro, carboxy, alkyl, alkoxy, haloalkyl, acyloxy, thioalkyl, sulfinylalkyl, sulfonylalkyl, hydroxyalkyl, aryl, substituted aryl, aralkyl, substituted aralkyl, heterocycle, substituted heterocycle, heterocyclealkyl, substituted heterocyclealkyl, —C(=O)OR$_8$, —OC(=O)R$_8$; —C(=O)NR$_8$R$_9$, —C(=O)NR$_8$OR$_9$, —SO$_c$R$_8$, —SO$_c$NR$_8$R$_9$, —NR$_8$SO$_c$R$_9$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(H$_2$)$_b$NR$_8$R$_9$, or heterocycle fused to phenyl; R$_8$, R$_9$, R$_{10}$ and R$_{11}$ are the same or different and at each occurrence independently hydrogen, alkyl, substituted alkyl, aryl, substituted aryl, aralkyl, substituted arylalkyl, heterocycle, substituted heterocycle, heterocyclealkyl or substituted heterocyclealkyl; or R$_8$ and R$_9$ taken together with the atom or atoms to which they are attached form a heterocycle or substituted heterocycle; a and b are the same or different and at each occurrence independently selected from 0, 1, 2, 3 or 4; and c is at each occurrence 0, 1 or 2.

In one embodiment, the composition according to the present invention does not comprise a compound of formula (VIIa) or a salt thereof:

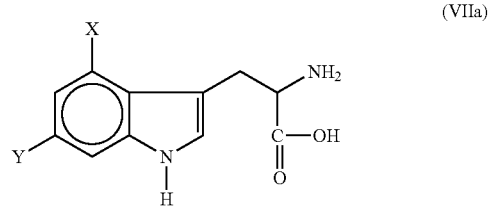

wherein X and Y are each independently selected from the group consisting of Cl, Br, F, CH$_3$ and CH$_2$CH$_3$.

In one embodiment, the composition according to the present invention does not comprise a compound of formula (VIIIa) or a salt thereof:

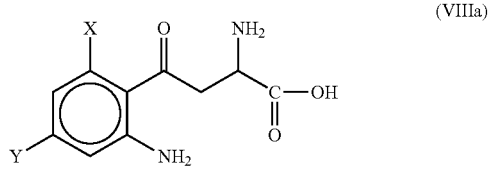

wherein X and Y are each independently selected from the group consisting of Cl, Br, F, CH$_3$ and CH$_2$CH$_3$.

In one embodiment, the composition according to the present invention does not comprise a compound of formula (VIIb) or a salt thereof:

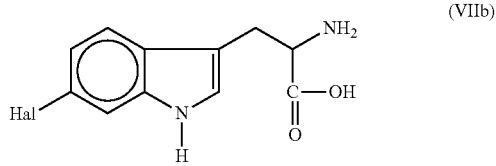

wherein Hal is an halogen atom.

In one embodiment, the composition according to the present invention does not comprise a compound of formula (VIIIb) or a salt thereof:

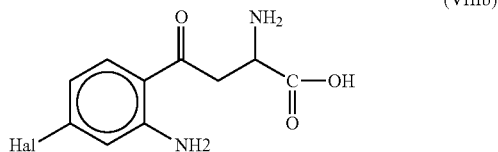
(VIIIb)

wherein Hal is an halogen atom.

In one embodiment, the composition according to the present invention does not comprise a compound of formula (IX) or a salt thereof:

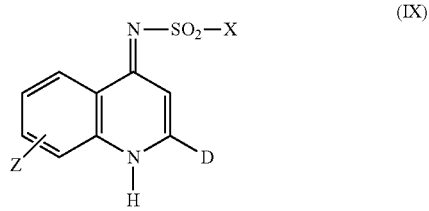
(IX)

wherein D is $C(O)OR_1$, $C(O)NR_1R_2$, wherein $R_1$ and $R_2$ are each independently hydrogen or $C_1$-$C_6$ alkyl; Z (which may be in positions 3, 5, 6, 7 or 8 and may represent up to 3 non-hydrogen substituents) is a substituent selected from the group consisting of hydrogen, —OH, halogen, —CN, —$NO_2$, $C_1$-$C_6$ alkyl, $C_1$-$C_6$ alkoxy, —$OCF_3$ and $CF_3$; X is one of the following substituents: —$(CY_2)_nCY_3$, —$(CT_2)_n CT_3$,

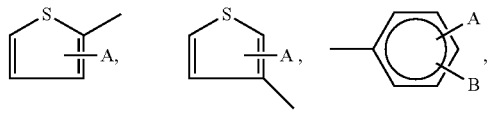

wherein Y is Cl; T is F; n is an integer from 0-3; A is a substituent selected from the group consisting of hydrogen, —OH, halogen, —CN, —$NO_2$, $C_1$-$C_6$ alkyl, $C_1$-$C_6$ alkoxy, —$CF_3$ and may be represented by up to 3 non-hydrogen substituents when B is hydrogen; when B is not hydrogen, then up to 2 A substituents may be present on the phenyl ring; when X is a thiophene ring, A may represent up to 2 non-hydrogen substituents which may be the same or different; B is one substituent selected from the group consisting of hydrogen, $C(O)OR_1$, $C(O)NR_1R_2$, $NH_2$, $NR_1R_2$, $NHC(O)R_3$, $NHC(O)OR_3$, $NHC(O)NHR_3$, NH—$SO_2$—$CF_3$, NH—$SO_2$—$C_6H_5$; in which $R_1$ and $R_2$ are as defined above and $R_3$ is $C_1$-$C_6$ alkyl; with the proviso: 1) that when D is $C(O)OCH_3$ and X is phenyl in which A is para-methyl and B is hydrogen, then Z is not hydrogen or a 5,7-dichloro substituent; 2) that when D is $C(O)OC_2H_5$ and X is phenyl in which A is para-methyl and B is hydrogen, then Z is not 6-methoxy, 7-methoxy or 5,8-dimethoxy; and 3) that when B is other than hydrogen, the total of A plus B may not be more than 3 substituents.

In one embodiment, the composition according to the present invention does not comprise a dipeptidyl peptidase IV inhibitor (DPP-IV inhibitor). Examples of DPP-IV inhibitor include, but are not limited to, sitagliptin, vildagliptin, saxagliptin, linagliptin, gemigliptin, anagliptin, teneligliptin, alogliptin, trelagliptin, omarigliptin, evogliptin, dutogliptin, berberine, lupeol and derivatives thereof.

Another object of the present invention is a pharmaceutical composition for use in treating epileptic diseases, disorders or conditions in a subject in need thereof comprising, consisting of or consisting essentially of probenecid or a pharmaceutically acceptable salt thereof as an active ingredient and at least one pharmaceutically acceptable excipient.

Suitable excipients include, but are not limited to, water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In addition, some excipients may include, without limitation, surfactants (e.g., hydroxypropylcellulose); suitable carriers such as, for example, solvents and dispersion media containing, for example, water, ethanol, polyol (e.g., glycerol, propylene glycol, liquid polyethylene glycol and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose; and the like.

Another object of the invention is a medicament for use in treating epileptic diseases, disorders or conditions in a subject in need thereof comprising, consisting or consisting essentially of probenecid or of a pharmaceutically acceptable salt thereof as active ingredient.

In one embodiment, the composition, the pharmaceutical composition or the medicament of the invention is to be administered systemically or locally.

In one embodiment, the composition, the pharmaceutical composition or the medicament of the invention is to be administered orally, buccally, by injection, by percutaneous administration, parenterally, intraperitoneal, by endoscopy, topically, transdermally, transmucosally, nasally, by inhalation spray, rectally, vaginally, intratracheally, and via an implanted reservoir.

In one embodiment, the composition, the pharmaceutical composition or the medicament of the invention is injected, preferably systemically injected. Examples of formulations adapted to systemic injections include, but are not limited to, liquid solutions or suspensions, solid forms suitable for solution in, or suspension in, liquid prior to injection.

Examples of systemic injections include, but are not limited to, intravenous, intratumoral, intracranial, intralymphatic, intraperitoneal, intramuscular, subcutaneous, intradermal, intraarticular, intrasynovial, intrasternal, intrathecal, intravesical, intrahepatic, intralesional, infusion techniques and perfusion. In another embodiment, when injected, the composition, the pharmaceutical composition or the medicament of the invention is sterile. Methods for obtaining a sterile pharmaceutical composition include, but are not limited to, GMP synthesis (GMP stands for "Good manufacturing practice").

In another embodiment, the composition, the pharmaceutical composition or the medicament of the invention is orally administered. Examples of formulations adapted to oral administration include, but are not limited to, solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet. Examples of liquid form adapted to oral administration include, but are not limited to, solutions, suspensions, drinkable solutions, elixirs, sealed phial, potion, drench, syrup and liquor.

In another embodiment, the composition, the pharmaceutical composition or the medicament of the invention is topically administered. Examples of formulations adapted to topical administration include, but are not limited to, sticks, lipsticks, waxes, creams, lotions, ointments, balms, gels, glosses, sunscreen preparations, cosmetics, masks, leave-on washes or cleansers, depilatory preparations and/or the like.

Topical administration characterizes the delivery, administration or application of the composition, the pharmaceutical composition or the medicament of the invention directly to the site of interest for a localized effect (generally onto one or more exposed or outer surfaces thereof, such as the outermost layer of the epidermis, which is exposed and visually observable), e.g., using hands, fingers or a wide variety of applicators (rollup, roll-on or other stick container, tube container, cotton ball, powder puff, Q-tip, pump, brush, mat, cloth and/or the like). The application may be made, e.g., by laying, placing, rubbing, sweeping, pouring, spreading and/or massaging into, or onto, the skin, or by any other convenient or suitable method. Preferably, topical administration is effected without any significant absorption of components of the composition into the subject's blood stream (to avoid a systemic effect).

The composition, the pharmaceutical composition or the medicament of the invention of the invention can be mixed to form white, smooth, homogeneous, opaque cream or lotion with, e.g., benzyl alcohol 1% or 2% (w/w) as a preservative, emulsifying wax, glycerin, isopropyl palmitate, lactic acid, purified water and sorbitol solution. In addition, the compositions can contain polyethylene glycol 400 (PEG 400). They can be mixed to form ointments with, e.g., benzyl alcohol 2% (w/w) as preservative, white petrolatum, emulsifying wax and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application.

In one embodiment of the invention, the composition, pharmaceutical composition or medicament of the invention may be used in conjunction with delivery systems that facilitate delivery of the agents to the central nervous system. For example, various blood brain barrier (BBB) permeability enhancers may be used to transiently and reversibly increase the permeability of the blood brain barrier to a treatment agent. Such BBB permeability enhancers include, but are not limited to, leukotrienes, bradykinin agonists, histamine, tight junction disruptors (e.g., zonulin, zot), hyperosmotic solutions (e.g., mannitol), cytoskeletal contracting agents, and short chain alkylglycerols (e.g., 1-O-pentylglycerol). Oral, sublingual, parenteral, implantation, nasal and inhalational routes can provide delivery of the active agent to the central nervous system. In some embodiments, the compounds of the present invention may be administered to the central nervous system with minimal effects on the peripheral nervous system.

The blood-brain barrier (BBB) is a physical barrier and system of cellular transport mechanisms between the blood vessels in the central nervous system (CNS) and most areas of the CNS itself. The BBB maintains homeostasis by restricting the entry of potentially harmful chemicals from the blood, and by allowing the entry of essential nutrients. However, the BBB can pose a formidable barrier to delivery of pharmacological agents to the CNS for treatment of disorders (such as epileptic diseases, disorders or conditions) or maintaining or enhancing normal and desirable brain functions, such as cognition, learning, and memory.

In one embodiment, the inhibitor, the composition, the pharmaceutical composition or the medicament is administered in a sustained-release form. In another embodiment, the composition, the pharmaceutical composition or the medicament comprises a delivery system that controls the release of the modulator.

In one embodiment, probenecid or a pharmaceutically acceptable salt thereof, the composition, the pharmaceutical composition or the medicament of the invention is to be administered at a dose determined by the skilled artisan and personally adapted to each subject. It will be understood that the total daily usage of probenecid or of a pharmaceutically acceptable salt thereof, the composition, pharmaceutical composition and medicament of the present invention will be decided by the attending physician within the scope of sound medical judgment. Dosage is adjusted to provide sufficient levels of probenecid or of a pharmaceutically acceptable salt thereof, the composition, the pharmaceutical composition or the medicament of the invention or to maintain the desired effect of reducing signs or symptoms of the targeted epileptic disease, disorder or condition, or reducing severity of the epileptic disease, disorder or condition. The specific therapeutically effective amount for any particular patient will depend upon a variety of factors including, but not limited to, the disease, disorder or condition being treated; the severity of the epileptic disease, disorder or condition (such as for example the frequency and duration of epileptic seizures); the prognosis of the disease; the localization of the seizures' initiation points; the specific composition employed; the time and frequency of administration, route of administration, the duration of the treatment; drugs used in combination or coincidental with probenecid or a pharmaceutically acceptable salt thereof, the composition, pharmaceutical composition or medicament of the invention; reaction sensitivities; tolerance/response to therapy; general health of the subject; age, weight, gender and diet of the subject; and like factors well known in the medical arts.

In one embodiment, a therapeutically effective amount of probenecid or of a pharmaceutically acceptable salt thereof, the composition, pharmaceutical composition or medicament of the invention is to be administered at least once a day, twice a day, at least three times a day.

In another embodiment, a therapeutically effective amount of probenecid or of a pharmaceutically acceptable salt thereof, the composition, pharmaceutical composition or medicament of the invention is to be administered every two, three, four, five, six days.

In another embodiment, a therapeutically effective amount of probenecid or of a pharmaceutically acceptable salt thereof, the composition, pharmaceutical composition or medicament of the invention is to be administered twice a week, every week, every two weeks, once a month.

In one embodiment of the invention, the daily amount of probenecid or of a pharmaceutically acceptable salt thereof, the composition, pharmaceutical composition or medicament of the invention to be administered to a subject ranges from about 25 mg/day to about 10 g/day, from about 50 mg/day to about 9 g/day, from about 75 mg/day to about 8 g/day, from about 100 mg/day to about 7 g/day, from about 200 mg/day to about 6 g/day, from about 300 mg/day to about 5 g/day, from about 400 mg/day to about 4 g/day, from about 500 mg/day to about 3 g/day, from about 550 mg/day to about 2 g/day, from about 600 mg/day to about 1.9 g/day, from about 650 mg/day to about 1.8 g/day, from about 700 mg/day to about 1.7 g/day, from about 750 mg/day to about 1.6 g/day, from about 800 mg/day to about 1.5 g/day, from about 850 mg/day to about 1.5 g/day, from about 900 mg/day to about 1.4 g/day, from about 950 mg/day to about 1.3 g/day, from about 1 g/day to about 1.3 g/day.

In one embodiment of the invention, the daily amount of probenecid or of a pharmaceutically acceptable salt thereof, the composition, pharmaceutical composition or medicament of the invention to be administered to a subject is about 25 mg/day, 50 mg/day, 75 mg/day, 100 mg/day, 200 mg/day, 300 mg/day, 400 mg/day, 500 mg/day, 600 mg/day, 700 mg/day, 800 mg/day, 900 mg/day, 1 g/day, 1.1 g/day, 1.2 g/day, 1.3 g/day, 1.4 g/day, 1.5 g/day, 1.6 g/day, 1.7 g/day, 1.8 g/day, 1.9 g/day, 2 g/day, 2.5 g/day, 3 g/day, 4 g/day or 5 g/day.

In one embodiment of the invention, the daily amount of probenecid or of a pharmaceutically acceptable salt thereof, the composition, pharmaceutical composition or medicament of the invention to be administered to a subject ranges from about 1 mg/kg/day to about 100 mg/kg/day, from about 2 mg/kg/day to about 90 mg/kg/day, from about 3 mg/kg/day to about 80 mg/kg/day, from about 4 mg/kg/day to about 70 mg/kg/day, from about 5 mg/kg/day to about 60 mg/kg/day, from about 6 mg/kg/day to about 50 mg/kg/day, from about 7 mg/kg/day to about 40 mg/kg/day, from about 8 mg/kg/day to about 35 mg/kg/day, from about 9 mg/kg/day to about 30 mg/kg/day, from about 10 mg/kg/day to about 25 mg/kg/day, from about 11 mg/kg/day to about 24 mg/kg/day, from about 12 mg/kg/day to about 23 mg/kg/day, from about 13 mg/kg/day to about 22 mg/kg/day, from about 14 mg/kg/day to about 21 mg/kg/day, from about 15 mg/kg/day to about 20 mg/kg/day, from about 16 mg/kg/day to about 19 mg/kg/day, from about 16 mg/kg/day to about 18 mg/kg/day.

In one embodiment of the invention, the daily amount of probenecid or of a pharmaceutically acceptable salt thereof, the composition, pharmaceutical composition or medicament of the invention to be administered to a subject is about 1 mg/kg/day, about 2 mg/kg/day, about 3 mg/kg/day, about 4 mg/kg/day, about 5 mg/kg/day, about 6 mg/kg/day, about 7 mg/kg/day, about 8 mg/kg/day, about 9 mg/kg/day, about 10 mg/kg/day, about 11 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, about 25 mg/kg/day, about 26 mg/kg/day, about 27 mg/kg/day, about 28 mg/kg/day, about 29 mg/kg/day, about 30 mg/kg/day.

In another embodiment, probenecid or a pharmaceutically acceptable salt thereof, the composition, pharmaceutical composition or medicament of the invention is to be administered at a dose ranging from about 1 mg to about 10 g, from about 10 mg to about 10 g, from about 10 mg to about 7.5 g, from about 25 mg to about 7.5 g, from about 50 mg to about 7.5 g, from about 75 mg to about 7.5 g, from about 100 mg to about 5 g, from about 200 mg to about 4 g, from about 300 mg to about 3 g, from about 500 mg to about 3 g, from about 750 mg to about 3 g, from about 750 mg to about 2 g, from about 800 mg to about 2 g, from about 900 mg to about 2 g, from about 900 mg to about 1.5 g, from about 1 g to about 1.4 g, or from about 1 g to about 1.3 g.

In another embodiment, probenecid or a pharmaceutically acceptable salt thereof, the composition, pharmaceutical composition or medicament of the invention is to be administered at a dose of about 1 mg, 10 mg, 25 mg, 50 mg, 75 mg, 100 mg, 200 mg, 300 mg, 400 mg, 500 mg, 600 mg, 700 mg, 800 mg, 900 mg, 1 g, 1.1 g, 1.2 g, 1.3 g, 1.4 g, 1.5 g, 1.6 g, 1.7 g, 1.8 g, 1.9 g, 2 g.

In one embodiment, the method of the invention is for a chronic treatment. In another embodiment, the method of the invention is for an acute treatment.

In one embodiment, probenecid or a pharmaceutically acceptable salt thereof, the composition, pharmaceutical composition or medicament of the invention is to be administered in a bolus injection, by continuous infusion, or in a combination of bolus injection and continuous infusion. The term "bolus injection" is understood to be an injection wherein the dose is delivered over a relatively short period of time. The term "continuous infusion" is understood to be an injection delivered, such as with an intravenous drip, wherein the dose is delivered in a metered manner over the period of time desired for probenecid therapy. In an embodiment, probenecid or a pharmaceutically acceptable salt thereof, the composition, pharmaceutical composition or medicament of the invention is to be administered via continuous infusion over a period of time ranging between about 30 min/day to about 24 hours/day. In another embodiment, probenecid or a pharmaceutically acceptable salt thereof, the composition, pharmaceutical composition or medicament of the invention is to be administered over a period of about 8 hours/day to about 24 hours/day. In some circumstances, probenecid or a pharmaceutically acceptable salt thereof, the composition, pharmaceutical composition or medicament of the invention is to be administered via continuous drip on at least one day and up to on seven days. In other circumstances, probenecid or a pharmaceutically acceptable salt thereof, the composition, pharmaceutical composition or medicament of the invention may be administered for even longer periods of times, such as on days over multiple weeks, months, or even years, as necessary to treat the symptoms in the subject. Thus, embodiments of the invention are directed to the long-term administration of probenecid or a pharmaceutically acceptable salt thereof, the composition, pharmaceutical composition or medicament of the invention to treat epileptic disease, disorder or condition and the associated symptoms of brain dysfunction.

In some instances, a combination of bolus injection with continuous infusion may be desired to a treat a subject. For example, a bolus injection may be utilized to deliver a loading dose, i.e., a dose of probenecid or of a pharmaceutically acceptable salt thereof to rapidly achieve a desired therapeutic level of probenecid or of a pharmaceutically acceptable salt thereof in the subject, and the continuous infusion may be utilized to maintain or even titrate the desired therapeutic levels over the desired duration of treatment. After the initial bolus injection, the subject may then require followed by maintenance administration or titration of probenecid or of a pharmaceutically acceptable salt thereof such as via continuous infusion for a period of time thereafter. In the alternative, maintenance administration of probenecid or of a pharmaceutically acceptable salt thereof may be accomplished with subsequent bolus injections. The continuous infusion of probenecid or of a pharmaceutically acceptable salt thereof is also useful in treating subjects with epileptic diseases, disorders or conditions.

The present invention further relates to a method for treating a neurological disorder in a subject in need thereof, comprising administering to the subject a therapeutically effective amount of probenecid or pharmaceutically acceptable salt thereof.

The present invention further relates to a method for inhibiting electrographic seizures in a subject in need thereof, comprising administering to the subject a therapeutically effective amount of probenecid or pharmaceutically acceptable salt thereof.

The present invention further relates to a method for inhibiting compulsive behaviors in a subject in need thereof, comprising administering to the subject a therapeutically effective amount of probenecid or pharmaceutically acceptable salt thereof.

The present invention further relates to a method for controlling clinical or electrographic seizures in a subject in need thereof, comprising administering to the subject a therapeutically effective amount of probenecid or pharmaceutically acceptable salt thereof.

The present invention further relates to a method for treating an epileptic disease, disorder or condition in a subject in need thereof, comprising administering to the subject a therapeutically effective amount of probenecid or pharmaceutically acceptable salt thereof.

The present invention further relates to the use of a therapeutically effective amount of probenecid or pharmaceutically acceptable salt thereof, for treating a neurological disorder in a subject in need thereof.

The present invention further relates to the use of a therapeutically effective amount of probenecid or pharmaceutically acceptable salt thereof, for inhibiting electrographic seizures in a subject in need thereof.

The present invention further relates to the use of a therapeutically effective amount of probenecid or pharmaceutically acceptable salt thereof, for inhibiting compulsive behaviors in a subject in need thereof.

The present invention further relates to the use of a therapeutically effective amount of probenecid or pharmaceutically acceptable salt thereof, for controlling clinical or electrographic seizures in a subject in need thereof.

The present invention further relates to the use of a therapeutically effective amount of probenecid or pharmaceutically acceptable salt thereof, for treating an epileptic disease, disorder or condition in a subject in need thereof.

The present invention further relates to the use of a therapeutically effective amount of probenecid or pharmaceutically acceptable salt thereof in the manufacture of a medicament, for the treatment of a neurological disorder in a subject in need thereof.

The present invention further relates to the use of a therapeutically effective amount of probenecid or pharmaceutically acceptable salt thereof in the manufacture of a medicament, for inhibiting electrographic seizures in a subject in need thereof.

The present invention further relates to the use of a therapeutically effective amount of probenecid or pharmaceutically acceptable salt thereof in the manufacture of a medicament, for inhibiting compulsive behaviors in a subject in need thereof.

The present invention further relates to the use of a therapeutically effective amount of probenecid or pharmaceutically acceptable salt thereof in the manufacture of a medicament, for controlling clinical or electrographic seizures in a subject in need thereof.

The present invention further relates to the use of a therapeutically effective amount of probenecid or pharmaceutically acceptable salt thereof in the manufacture of a medicament, for the treatment of an epileptic disease, disorder or condition in a subject in need thereof.

The present invention further relates to a method for inducing a decrease of the frequency and/or duration of ictal discharges, preferably a decrease of the frequency of at least 25%, preferably at least 30%, 40%, 50%, 60%, 70%, 80%, 90% or more, and/or a decrease of the duration of at least 25%, preferably at least 30%, 40%, 50%, 60%, 70%, 80%, 90% or more.

The present invention relates to a method for inducing a decrease of the frequency and/or duration of spontaneous seizures, preferably a decrease of the frequency of at least 25%, preferably at least 30%, 40%, 50%, 60%, 70%, 80%, 90% or more, and/or a decrease of the duration of at least 25%, preferably at least 30%, 40%, 50%, 60%, 70%, 80%, 90% or more.

EXAMPLES

Materials and Methods

Preparation of Human Cortical Slices

The resected cortical block was prepared according to Dossi et al. (J Vis Exp. 2014 Oct. 26; (92):e51870). Briefly, post-surgical tissue was transported in a cold solution containing (in mM) 250 D-sucrose, 25 $NaHCO_3$, 3 KCl, 1 $CaCl_2$, 10 $MgCl_2$ and 10 D-glucose, and oxygenated with carbogen (95% $O_2$ and 5% $CO_2$). Meninges, blood clots and vessels were gently removed and transverse cortical slices (400 μm-thick) were cut with a vibratome (HM650V, Microm Microtech, France). They were maintained at 37° C., equilibrated with 95% $O_2$ and 5% $CO_2$, in an interface chamber, continuously perfused with an artificial cerebrospinal fluid (ACSF) containing (in mM) 124 NaCl, 3 KCl, 26 NaHCO$_3$, 1.6 CaCl$_2$, 1.3 MgCl$_2$ and 10 D-glucose at 2 ml/min, for at least 1 hour before recording.

Multi-Electrode Array (MEA) Recordings

Cortical slices were transferred on planar MEA petri dishes (200-30 ITO electrodes, organized in a 12×12 matrix, with internal reference, 30 µm diameter and 200 µm inter-electrode distance; Multichannel Systems, Germany). They were kept in place using a platinum anchor and continuously perfused at a rate of 5-6 ml/min with ACSF.

Pictures of cortical slices on MEAs were acquired with a video microscope table (MEA-VMT1; Multichannel Systems, Germany) through MEA_Monitor software (Multichannel Systems, Germany) to identify the location of the electrodes relatively to the pial surface of the slices. Data were sampled at 10 kHz and the slice activity was recorded at 37° C. by a MEA2100-120 system (bandwidth 1-3000 Hz, gain 5×; Multichannel Systems, Germany) through MC_Rack 4.5.1 software (Multichannel systems, Germany) The activity of the slices was recorded in ACSF containing (in mM) 124 NaCl, 3 KCl, 26 NaHCO$_3$, 1.6 CaCl$_2$, 1.3 MgCl$_2$ and 10 D-glucose (Ct ACSF) and in high potassium, magnesium-free pro-epileptic ACSF containing (in mM) 6 KCl, 0 Mg$^{2+}$ (6K 0Mg-ACSF).

Mouse Model of Temporal Lobe Epilepsy

Six weeks old C57BL/6j male mice were injected unilaterally with kainate (KA; 0.05 µl, 20 mM in saline) at a rate of 0.5 µl/min in the CA1 area of the right hippocampus (−2 mm anteroposterior, +1.5 mm lateral, −1.4 mm dorsoventral) by mean of a stereotaxic apparatus and a cannula (0.29 mm diameter) connected to a precision pump. Mice were then left 3 weeks for settling of the chronic epileptic phenotype.

Telemetric EEG and Video Recording

EEG experiments were carried out using wireless ETA-F 10 transmitters (DataSciences International, USA) for chronic EEG recording and video monitoring 3 weeks after KA injection. After anesthesia (ketamine, 95 mg/kg; xylazine, 10 mg/kg; i.p.), a 1 cm midline sagittal incision was made starting above the skull midline and extending along the neck to create a pocket for subcutaneous placement of the transmitter along the dorsal flank of the animal. The recording flexible electrodes (stereotaxic coordinates: −2 mm anteroposterior, +1.5 mm and −1.5 mm lateral) were implanted subdurally through small holes drilled in the skull and held in place with dental cement. Mice were implanted with wireless ETA-F10 transmitters 2 weeks after the KA injection and were allowed to recover for 7 days before recording.

EEG signal was collected through DSI radiofrequency receivers placed under each cage. EEG data were acquired at a sampling rate of 200 Hz using the DSI Dataquest A.R.T. system (version 4.33). To assess therapeutic potential of probenecid, KA mice were recorded with ETA-F10 DSI EEG electrodes for 48 h in their home cage, injected with probenecid (200 mg/kg in corn oil, Sigma-Aldrich; i.p.) and recorded for 24 hours post-treatment. Analysis of seizures was performed using the NeuroScore software (Data Sciences International, USA); seizures were detected on the EEG as spike trains with a minimal amplitude of 1.5× baseline and a minimal duration of 5 s at a frequency ≥1 Hz (Bergstrom et al., Sci Rep. 2013; 3:1483. doi: 10.1038/srep01483). Artifacts were automatically detected using a high detection threshold and removed manually.

Results

Probenecid Completely Blocked Ictal Discharges in Human Epileptic Cortical Tissue To investigate whether probenecid medication could be used as a treatment for epileptic seizures, the electrophysiological activity of human epileptic cortical slices was recorded in pro-epileptic conditions, before and after probenecid administration (1 mM, 30 minutes).

The treatment with probenecid fully inhibited ictal-like discharges (IDs) in 5 out of 6 human cortical slices, while it halved ID duration in the remaining slice (Table 1, FIGS. 1A and B).

TABLE 1

| | Control | Probenecid | p |
|---|---|---|---|
| | n = 6 | | |
| ID frequency | 0.34 ± 0.06 IDs/min | 0.03 ± 0.03 IDs/min | 0.0313 |
| ID duration | 59.45 ± 12.39 s | 7.59 ± 7.59 s | 0.0313 |

Importantly, such control occurs in human tissues from various pathological conditions, such as gliomas, focal cortical dysplasia and dysembryoplastic neuroepithelial tumour (DNET). This suggests that probenecid modulation of ictal activity is likely a general mechanism underlying human seizures associated with various diseases.

Finally, when ID-like events disappeared, only small amplitude interictal discharges (IIDs) or high amplitude discharges previously described as pre-ictal discharges (PIDs) persisted (FIGS. 1A and B).

Figure 1C:
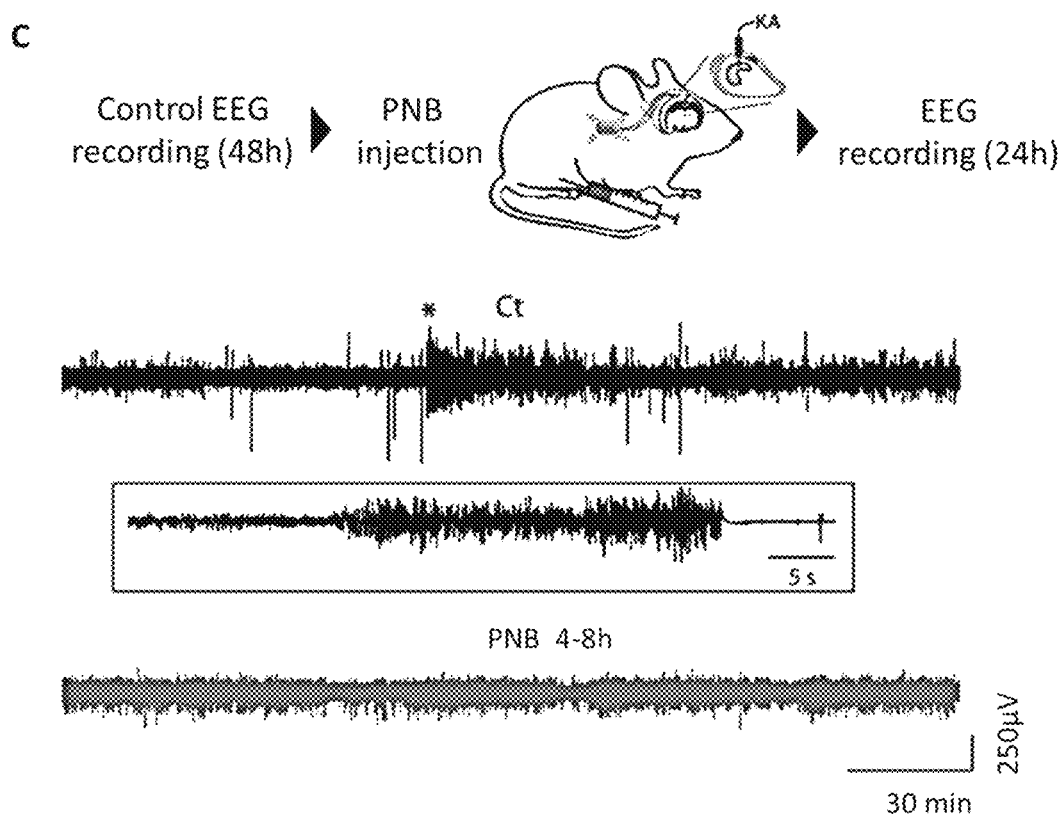
FIG. 1C (Left), is a schematic representation of the experimental protocol: EEG from KA mice was recorded for 48 hours before a single intraperitoneal injection of PBN (200 mg/kg) and 24 h after. (Right), are examples of 4 h EEG recordings before (black) and 4-8 h after PBN treatment (grey). The seizure observed in Ct and indicated by an asterisk is zoomed in the rectangle.
Figure 1D:
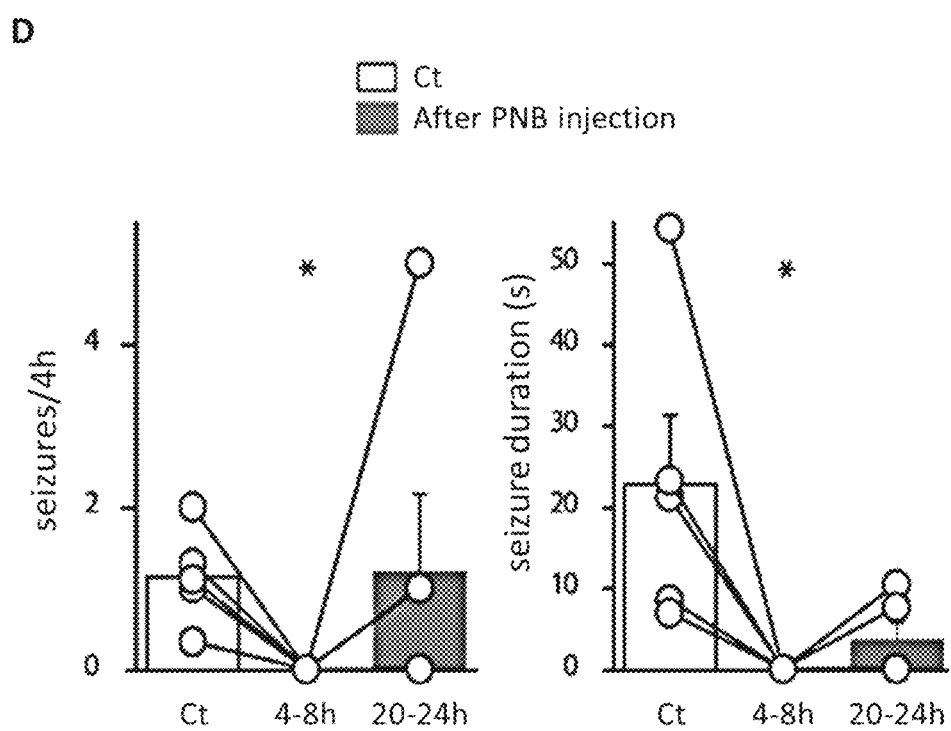
FIG. 1D is a graph depicting the quantification of PBN effect on seizure frequency and duration in Ct, 4-8 h and 20-24 h post-treatment (p=0.0370 and 0.0247 for frequency and duration, respectively; n=5, Friedman test with Dunn post hoc test). Asterisks indicate statistical significance (*, $p<0.05$).

Probenecid Completely Blocked Spontaneous Epileptic Seizures in the Kainate Mouse Model of Temporal Lobe Epilepsy To further assess the therapeutic potential of probenecid, we tested the in vivo effect of probenecid i.p. in a kainate (KA) mouse model of chronic temporal lobe epilepsy. To do so, electroencephalogram (EEG) of KA mice were recorded before (48 hours) and after (24 hours) probenecid administration (200 mg/kg) (FIG. 1C).

A single probenecid injection completely blocked spontaneous seizures 4 to 8 hours post-treatment (in all mice tested). Seizures then reappeared in 2 of 5 mice 20-24 hours post-treatment, however with significantly shorter duration (Table 2, FIGS. 1C and D).

TABLE 2

| | | Probenecid | P |
|---|---|---|---|
| | | n = 5 | |
| Seizure frequency | 48 h pre-treatment | 1.15 ± 0.27 seizures/4 h | 0.0370 |
| | 4-8 h post-treatment | no seizure detected | |
| | 20-24 h post-treatment | 1.2 ± 0.97 seizure/4 h | |
| Seizure duration | 48 h pre-treatment | 22.81 ± 8.51 s | 0.0247 |
| | 4-8 h post-treatment | no seizure detected | |
| | 20-24 h post-treatment | 3.6 ± 2.25 s | |

Altogether, these data show that probenecid, the well-established FDA and EMA-approved uricosuric agent traditionally used to treat gout (Hediger et al., Physiology (Bethesda). 2005 April; 20:125-33), can also be used as a therapy for human epilepsy and epileptic syndromes.

The invention claimed is:

1. A method for treating focal epilepsy in a human subject in need thereof, said focal epilepsy being characterized by an occurrence of spontaneous and recurrent focal seizures, the method comprising administering to the human subject a pharmaceutical composition consisting essentially of probenecid or a pharmaceutical acceptable salt thereof, wherein probenecid or the pharmaceutical acceptable salt thereof controls focal seizures in said human subject, and wherein probenecid or the pharmaceutical acceptable salt thereof is the only therapeutic agent administered to said human subject.

2. The method according to claim 1, wherein the focal epilepsy is selected from the group consisting of familial epilepsy, genetic epilepsy, structural/metabolic epilepsy and epilepsies with unknown cause.

3. The method according to claim 1, wherein the focal epilepsy is brain tumor-related epilepsy.

4. The method according to claim 1, wherein the focal epilepsy is a malformation of cortical development (MCD)-related epilepsy.

5. The method according to claim 1, wherein the focal epilepsy is a neurodegenerative-related epilepsy.

6. The method according to claim 1, wherein the focal epilepsy is a dysimmune epilepsy.

7. The method according to claim 1, wherein the human subject is suffering from a treatment-resistant focal epilepsy.

8. The method according to claim 1, wherein said human subject is a child.

9. The method according to claim 1, wherein said human subject is an adult.

10. The method according to claim 1, wherein probenecid or the pharmaceutical acceptable salt thereof is administered to the human subject at a dose ranging from 1 mg/kg/day to 100 mg/kg/day.

11. The method according to claim 1, wherein probenecid or the pharmaceutical acceptable salt thereof is administered orally or by injection.

12. The method according to claim 1, wherein probenecid or the pharmaceutical acceptable salt thereof is comprised within a pharmaceutical composition also comprising a pharmaceutically acceptable carrier or diluent.

13. The method according to claim 1, wherein probenecid or the pharmaceutical acceptable salt thereof is comprised within a medicament.

* * * * *